(12) United States Patent
Cho et al.

(10) Patent No.: US 10,456,114 B2
(45) Date of Patent: Oct. 29, 2019

(54) METHOD AND ULTRASOUND APPARATUS FOR DISPLAYING DIFFUSION BOUNDARY OF MEDICINE

(71) Applicants: SAMSUNG MEDISON CO., LTD., Hongcheon-gun, Gangwon-do (KR); SAMSUNG ELECTRONICS CO., LTD., Suwon-si, Gyeonggi-do (KR)

(72) Inventors: Eun-mi Cho, Hongcheon-gun (KR); Jung-taek Oh, Seoul (KR); Eun-yeong Kim, Hongcheon-gun (KR)

(73) Assignees: Samsung Medison Co., Ltd., Hongcheon-gun, Gangwon-do (KR); Samsung Electronics Co., Ltd., Suwon-si, Gyeonggi-do (KR)

( * ) Notice: Subject to any disclaimer, the term of this patent is extended or adjusted under 35 U.S.C. 154(b) by 655 days.

(21) Appl. No.: 14/656,642

(22) Filed: Mar. 12, 2015

(65) Prior Publication Data
US 2015/0257741 A1    Sep. 17, 2015

(30) Foreign Application Priority Data

Mar. 12, 2014  (KR) .......................... 10-2014-0029270

(51) Int. Cl.
*A61B 8/08* (2006.01)
*A61B 5/00* (2006.01)
(Continued)

(52) U.S. Cl.
CPC .......... *A61B 8/5246* (2013.01); *A61B 5/4848* (2013.01); *A61B 8/0833* (2013.01);
(Continued)

(58) Field of Classification Search
CPC ..... A61B 8/5246; A61B 8/0833; A61B 8/469; A61B 8/5223; A61B 8/463; A61B 8/481;
(Continued)

(56) References Cited

U.S. PATENT DOCUMENTS 5,860,931 A * 1/1999 Chandler ................. A61B 8/06
                                                         600/458
6,740,039 B1 * 5/2004 Rafter .................... A61B 8/463
                                                         600/439
(Continued)

FOREIGN PATENT DOCUMENTS

CN    101491449 A    7/2009
CN    102472738 B    8/2014
(Continued)

OTHER PUBLICATIONS

Extended European Search Report issued in Application No. 14196257.1 dated Aug. 11, 2015.
(Continued)

*Primary Examiner* — Thomas J Hong
*Assistant Examiner* — Helene Bor
(74) *Attorney, Agent, or Firm* — Morgan, Lewis & Bockius LLP

(57) ABSTRACT

Provided is a method of marking a diffusion boundary of medicine, the method performed by an ultrasound apparatus and including operations of obtaining first B mode image data and first Doppler data about a target object to which the medicine is injected; detecting a first area of the target object from which the first Doppler data is obtained; determining a first diffusion boundary of the medicine, based on the first area; and marking the first diffusion boundary of the medicine on a B mode image that is generated by using the first B mode image data.

14 Claims, 19 Drawing Sheets

(51) Int. Cl.
*A61B 8/00* (2006.01)
*G06T 7/00* (2017.01)

(52) U.S. Cl.
CPC .............. *A61B 8/463* (2013.01); *A61B 8/481* (2013.01); *A61B 8/488* (2013.01); *A61B 8/5223* (2013.01); *G06T 7/0012* (2013.01); *A61B 8/469* (2013.01); *G06T 2207/10132* (2013.01); *G06T 2207/30004* (2013.01)

(58) Field of Classification Search
CPC .................. A61B 8/488; A61B 5/4839; G06T 2207/30004; G06T 2207/10132; G06T 7/0012; A61M 37/0092; A61N 7/00
See application file for complete search history.

(56) References Cited

U.S. PATENT DOCUMENTS

| | | | |
|---|---|---|---|
| 8,524,505 B2 | 9/2013 | Kono et al. | |
| 2004/0138563 A1 | 7/2004 | Moehring et al. | |
| 2005/0283075 A1* | 12/2005 | Ma | G01S 15/8979 600/441 |
| 2008/0009737 A1 | 1/2008 | Takimoto et al. | |
| 2008/0214934 A1 | 9/2008 | Lee | |
| 2009/0187103 A1* | 7/2009 | Guracar | A61B 8/06 600/439 |
| 2009/0299191 A1 | 12/2009 | Hyun et al. | |
| 2011/0270087 A1 | 11/2011 | Yoshida et al. | |
| 2012/0310085 A1 | 12/2012 | Herweck et al. | |
| 2015/0141822 A1* | 5/2015 | Miyauchi | G06T 7/0012 600/438 |

FOREIGN PATENT DOCUMENTS

| | | |
|---|---|---|
| EP | 2 082 689 A1 | 7/2009 |
| JP | 2013-005994 A | 1/2013 |
| KR | 2003-0036137 A | 5/2003 |
| KR | 10-2009-0123363 A | 12/2009 |

OTHER PUBLICATIONS

Chinese Office Action dated Jan. 3, 2019 issued in Chinese Patent Application No. 201510108681.8 (with English translation).
Chinese Office Action dated May 27, 2019 issued in Chinese Patent Application No. 201510108681.8 (with English translation).

* cited by examiner

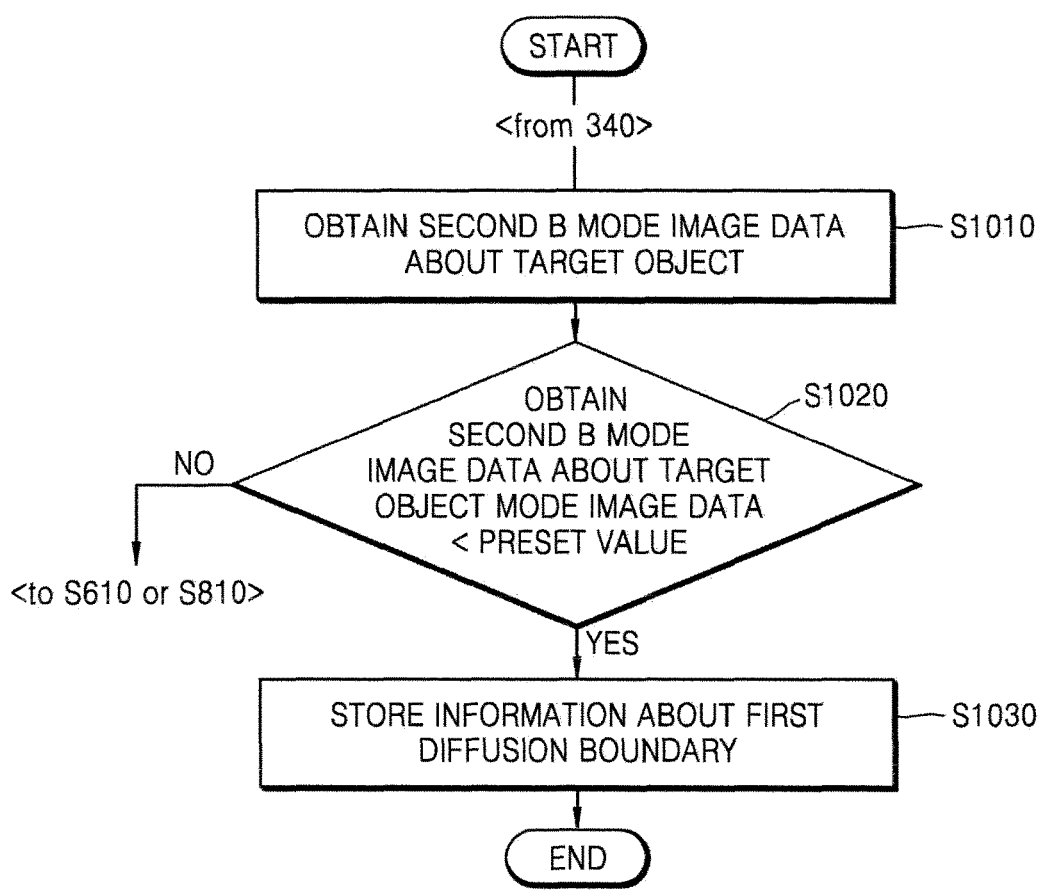

METHOD AND ULTRASOUND APPARATUS FOR DISPLAYING DIFFUSION BOUNDARY OF MEDICINE

RELATED APPLICATION

This application claims the benefit of Korean Patent Application No. 10-2014-0029270, filed on Mar. 12, 2014, in the Korean Intellectual Property Office, the disclosure of which is incorporated herein in its entirety by reference.

BACKGROUND

1. Field

One or more embodiments of the present invention relate to a method and ultrasound apparatus for displaying a diffusion boundary of medicine that is injected into a target object via a needle.

2. Description of the Related Art

An ultrasound diagnosis apparatus transmits an ultrasound signal from a body surface of a target object to a predetermined part inside a human body, and obtains an image of a cross-section of or a blood flow in a soft tissue by using information of the ultrasound signal that is reflected from a tissue inside the human body.

The ultrasound diagnosis apparatus is advantageous in that the ultrasound diagnosis apparatus is small, inexpensive, and capable of displaying an image in real-time. Also, the ultrasound diagnosis apparatus is safe without a risk of radioactivity due to an X-ray or the like, such that the ultrasound diagnosis apparatus may be widely used with other image diagnosis apparatuses such as an X-ray diagnosis apparatus, a computerized tomography (CT) scanner, a magnetic resonance image (MRI) apparatus, or a nuclear medicine diagnosis apparatus.

The ultrasound diagnosis apparatus may provide an image of a needle that is used for a biopsy or an image of a needle that injects medicine into an examinee.

SUMMARY

One or more embodiments of the present invention include a method of displaying a diffusion boundary of medicine by using an ultrasound apparatus, so that a user may recognize a diffusion position of the medicine that is injected into a target object via a needle.

Additional aspects will be set forth in part in the description which follows and, in part, will be apparent from the description, or may be learned by practice of the presented embodiments.

According to one or more embodiments of the present invention, a method of marking a diffusion boundary of medicine, the method performed by an ultrasound apparatus, includes operations of obtaining first B mode image data and first Doppler data about a target object to which the medicine is injected; detecting a first area of the target object from which the first Doppler data is obtained; determining a first diffusion boundary of the medicine, based on the first area; and marking the first diffusion boundary of the medicine on a B mode image that is generated by using the first B mode image data.

The first Doppler data may include at least one of color Doppler image data and power Doppler image data.

When a speed value included in the first Doppler data is equal to or greater than a threshold value, the operation of detecting the first area may include an operation of detecting the first area from which the first Doppler data is obtained.

In the operation of determining the first diffusion boundary, an outside area of the first area from which the first Doppler data is obtained may be determined as the first diffusion boundary of the medicine.

The operation of determining the first diffusion boundary may include operations of detecting a partial area of the first area where a speed value included in the first Doppler data is equal to or greater than a threshold value; and determining an outside area of the partial area, as the first diffusion boundary of the medicine.

The operation of marking the first diffusion boundary may include an operation of marking the first diffusion boundary of the medicine by using a line having a preset form.

The operation of marking the first diffusion boundary may include an operation of transparently or translucently displaying a first Doppler image that is generated based on the first Doppler data.

The method may further include operations of obtaining second Doppler data about the target object after an elapse of a preset time; and detecting a second area from which the second Doppler data is obtained.

The method may further include operations of determining a second diffusion boundary of the medicine, based on the second area; and marking the first diffusion boundary of the medicine and the second diffusion boundary of the medicine on the B mode image.

The method may further include operations of determining a third area by combining the first area and the second area; determining an outside area of the third area, as a third diffusion boundary of the medicine; and marking the third diffusion boundary of the medicine on the B mode image.

The operation of marking the first diffusion boundary may include operations of receiving an input of selecting a region of interest in the B mode image; and marking the first diffusion boundary in the region of interest.

When Doppler data about the target object is no longer obtained, the method may further include an operation of storing information about the first diffusion boundary.

The method may further include operations of obtaining second B mode image data about the target object; comparing the first B mode image data and the second B mode image data; and when a similarity between the first B mode image data and the second B mode image data is less than a preset value, storing information about the first diffusion boundary.

The method may further include an operation of providing, on the B mode image, at least one of numerical data about a diffusion range of the medicine, and comparison data obtained by comparing an estimated diffusion range of the medicine with an actual diffusion range of the medicine.

According to one or more embodiments of the present invention, a method of marking a diffusion boundary of medicine, the method performed by an ultrasound apparatus, includes operations of obtaining a first B mode image and a second B mode image of a target object to which the medicine is injected; comparing a first speckle pattern included in the first B mode image with a second speckle pattern included in the second B mode image; estimating a first movement path of at least one speckle included in the first B mode image, based on a result of the comparing; determining a first diffusion boundary of the medicine, based on the first movement path of the at least one speckle; and marking the first diffusion boundary of the medicine on the second B mode image.

The operation of comparing may include an operation of obtaining a correlation between the first speckle pattern and the second speckle pattern.

The operation of comparing may include operations of receiving an input of selecting a region of interest in the target object; and comparing the first speckle pattern included in the region of interest and the second speckle pattern included in the region of interest.

The operation of marking the first diffusion boundary may include an operation of marking the first diffusion boundary in the region of interest.

The operation of determining the first diffusion boundary may include operations of determining a first movement area including the first movement path of the at least one speckle; and determining an outside area of the first movement area, as the first diffusion boundary of the medicine.

The operation of determining the outside area may include operations of determining whether the first movement area is equal to or greater than a preset area; and when the first movement area is equal to or greater than the preset area, determining the outside area of the first movement area, as the first diffusion boundary of the medicine.

The operation of marking the first diffusion boundary may include an operation of marking the first diffusion boundary of the medicine by using a line having a preset form.

The operation of marking the first diffusion boundary may include an operation of transparently or translucently displaying a speckle tracking image that is generated based on a movement path of the at least one speckle.

The method may further include operations of obtaining a third B mode image of the target object; and estimating a second movement path of at least one speckle included in the second B mode image, based on a result of comparison between the second speckle pattern included in the second B mode image and a third speckle pattern included in the third B mode image.

The method may further include operations of determining a second diffusion boundary of the medicine, based on the second movement path; and marking the second diffusion boundary of the medicine on the third B mode image.

When a movement distance of the at least one speckle included in the second B mode image is less than a threshold value, the method may further include an operation of storing information about the first diffusion boundary.

The method may further include operations of comparing the second B mode image with the third B mode image; and when a similarity between the second B mode image and the third B mode image is less than a preset value, storing information about the first diffusion boundary.

The method may further include an operation of providing, on the second B mode image, at least one of numerical data about a diffusion range of the medicine, and comparison data obtained by comparing an estimated diffusion range of the medicine with an actual diffusion range of the medicine.

According to one or more embodiments of the present invention, an ultrasound apparatus includes an ultrasound image data obtainer configured to obtain first B mode image data and first Doppler data about a target object to which the medicine is injected; a controller configured to detect a first area of the target object from which the first Doppler data is obtained, and determine a first diffusion boundary of the medicine, based on the first area; and a display configured to mark the first diffusion boundary of the medicine on a B mode image that is generated by using the first B mode image data.

According to one or more embodiments of the present invention, an ultrasound apparatus includes an ultrasound image data obtainer configured to obtain a first B mode image and a second B mode image of a target object to which the medicine is injected; a controller configured to compare a first speckle pattern included in the first B mode image with a second speckle pattern included in the second B mode image, estimate a first movement path of at least one speckle included in the first B mode image, based on a result of the comparing, and determine a first diffusion boundary of the medicine, based on the first movement path of the at least one speckle; and a display configured to mark the first diffusion boundary of the medicine on the second B mode image.

BRIEF DESCRIPTION OF THE DRAWINGS

These and/or other aspects will become apparent and more readily appreciated from the following description of the embodiments, taken in conjunction with the accompanying drawings in which:

FIG. 10 is a flowchart of a method of storing information about a diffusion boundary of medicine, the method performed by the ultrasound apparatus, according to an embodiment of the present invention;

DETAILED DESCRIPTION

Figure 1:
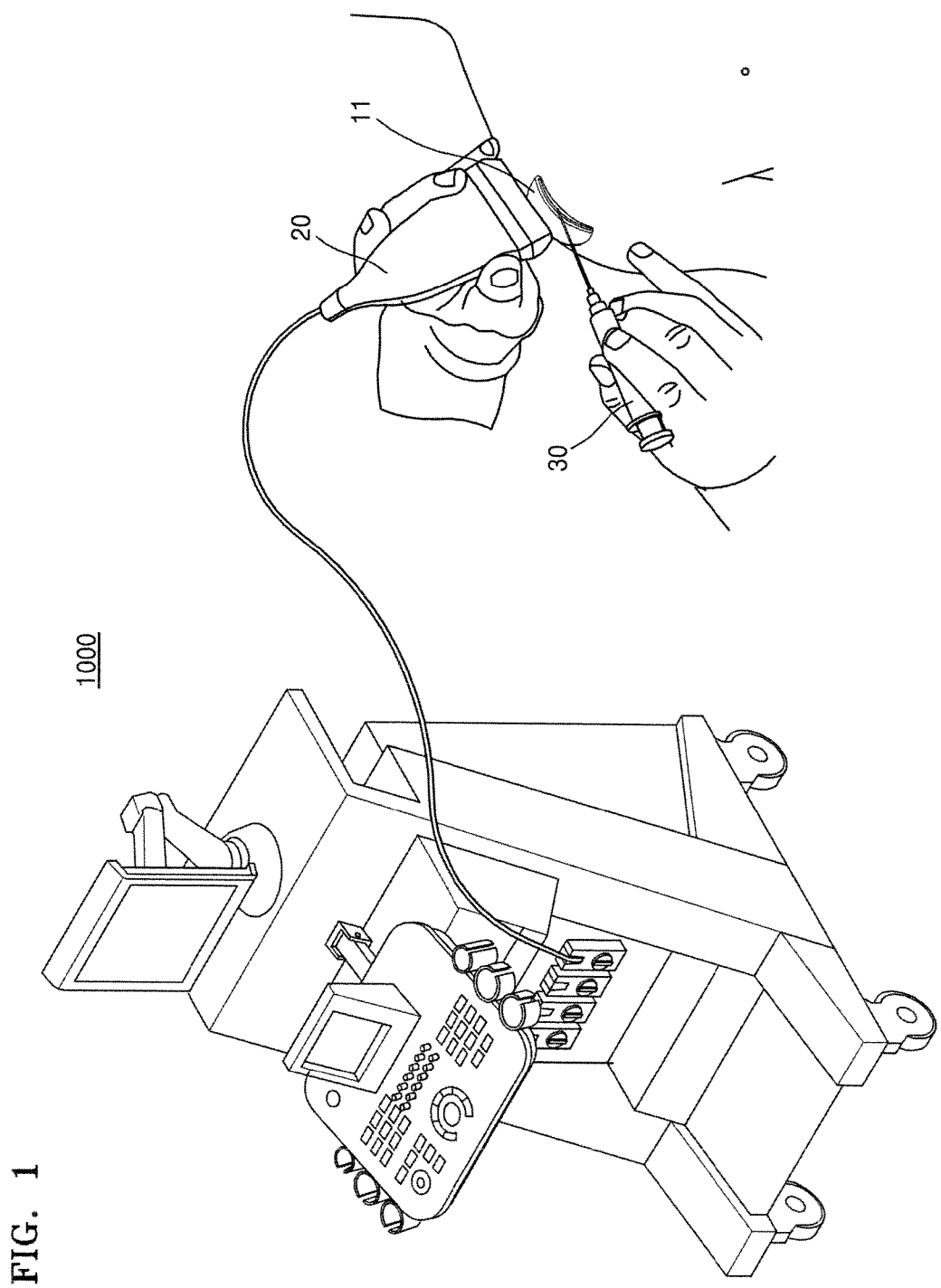
FIG. 1 illustrates a system for injecting medicine into a target object by using an ultrasound apparatus.

All terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant, and in this case, the meaning of the selected terms will be described in detail in the detailed description of the invention. Thus, the terms used herein have to be defined based on the meaning of the terms together with the description throughout the specification.

Also, when a part "includes" or "comprises" an element, unless there is a particular description contrary thereto, the part can further include other elements, not excluding the other elements. In the following description, terms such as "unit" and "module" indicate a unit for processing at least one function or operation, wherein the unit and the block may be embodied as hardware or software or embodied by combining hardware and software.

Throughout the specification, "ultrasound image" indicates an image of a target object which is obtained by using an ultrasound signal. The target object may be a part of a human body. For example, the target object may include organs such as the liver, the heart, the brain, the breast, the abdominal region, the nuchal translucency (NT), the shoulder muscle, a fetus, or the like.

The ultrasound image may vary in different forms. For example, the ultrasound image may be, but is not limited to, at least one of an image obtained during a brightness mode (hereinafter, referred to as "B mode image") indicating brightness as magnitude of an ultrasound echo signal that is reflected from the target object; a color Doppler image indicating a color as speed of a moving target object by using a Doppler effect; a spectral Doppler image indicating a spectrum image of a moving target object by using a Doppler effect; a power Doppler image indicating a color as intensity of a Doppler signal or the number of structures (e.g., the number of red corpuscles in blood); an image obtained during a motion mode (hereinafter, referred to as "M mode image") indicating motion of a target object at a predetermined position according to time; and an image obtained during an elasticity mode (hereinafter, referred to as "elasticity mode image") indicating a difference between a reaction when compression is applied to a target object and a reaction when compression is not applied to the target object. Also, in one or more embodiments of the present invention, the ultrasound image may be a two-dimensional (2D) image, a three-dimensional (3D) image, or a four-dimensional (4D) image.

Throughout the specification, a "user" may be a medical expert including a doctor, a nurse, a medical laboratory technologist, a sonographer, or the like.

Hereinafter, one or more embodiments of the present invention will be described in detail with reference to the attached drawings. The invention may, however, be embodied in many different forms, and should not be construed as being limited to the embodiments set forth herein; rather, these embodiments are provided so that this disclosure will be thorough and complete, and will fully convey the concept of the invention to those skilled in the art.

In the following description, well-known functions or constructions are not described in detail since they would obscure the invention with unnecessary detail, and like reference numerals in the drawings denote like or similar elements throughout the specification.

As used herein, the term "and/or" includes any and all combinations of one or more of the associated listed items. Expressions such as "at least one of," when preceding a list of elements, modify the entire list of elements and do not modify the individual elements of the list.

FIG. 1 illustrates a system for injecting medicine into a target object by using an ultrasound apparatus 1000.

As illustrated in FIG. 1, the ultrasound apparatus 1000 may transmit an ultrasound signal to the target object via a probe 20. Then, the ultrasound apparatus 1000 may receive an ultrasound echo signal reflected from the target object via the probe 20 and thus may generate an ultrasound image of the target object.

For example, when the medicine is injected into a bursa 11 via a needle 30, the ultrasound apparatus 1000 may convert intensity of the ultrasound echo signal, which is reflected from the target object including the bursa 11, into a brightness value, and thus may obtain a 2D B mode image of the target object.

Also, when the ultrasound apparatus 1000 operates during its Doppler mode, the ultrasound apparatus 1000 may obtain a Doppler signal that is generated when the medicine diffuses. The Doppler signal means a signal having a Doppler frequency. The Doppler frequency indicates a difference between a frequency of the ultrasound echo signal and a frequency of the ultrasound signal transmitted to the target object. The ultrasound apparatus 1000 may generate a Doppler image related to the diffusion of the medicine, by using the Doppler signal. This will be described in detail with reference to FIG. 2.

Figure 2:
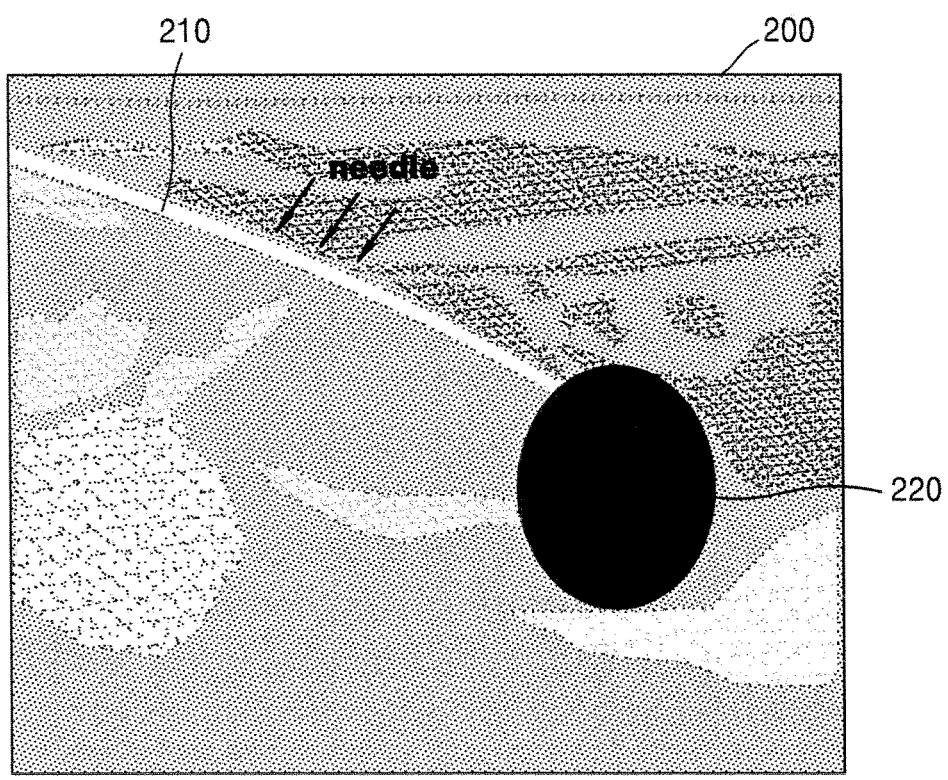
FIG. 2 illustrates an ultrasound image obtained by using the ultrasound apparatus, according to an embodiment of the present invention.

FIG. 2 illustrates an ultrasound image obtained by using the ultrasound apparatus 1000, according to an embodiment of the present invention.

As illustrated in FIG. 2, the ultrasound apparatus 1000 may display a 2D B mode image 200 of a target object to which medicine is injected via the needle 30. The 2D B mode image 200 may show an insertion path 210 of the needle 30. Thus, a user may recognize an inserted position of the needle 30 on the 2D B mode image 200.

Also, the ultrasound apparatus 1000 may display the 2D B mode image 200 after overlapping a Doppler image 220 on the 2D B mode image 200. Here, the Doppler image 220 indicates an imaged Doppler signal that is generated due to a diffusion of the medicine that was injected from a tip of the needle 30 into the target object. Thus, the user may recognize a diffusion range of the medicine on the 2D B mode image 200.

However, since the Doppler image 220 is generally imaged by using a specific color, it is difficult for the user to exactly recognize a structure behind the Doppler image 220. Thus, hereinafter, a method will be described in detail with reference to FIG. 3, and by using the method, a user may check whether the medicine is correctly injected into a target structure in the target object.

Figure 3:
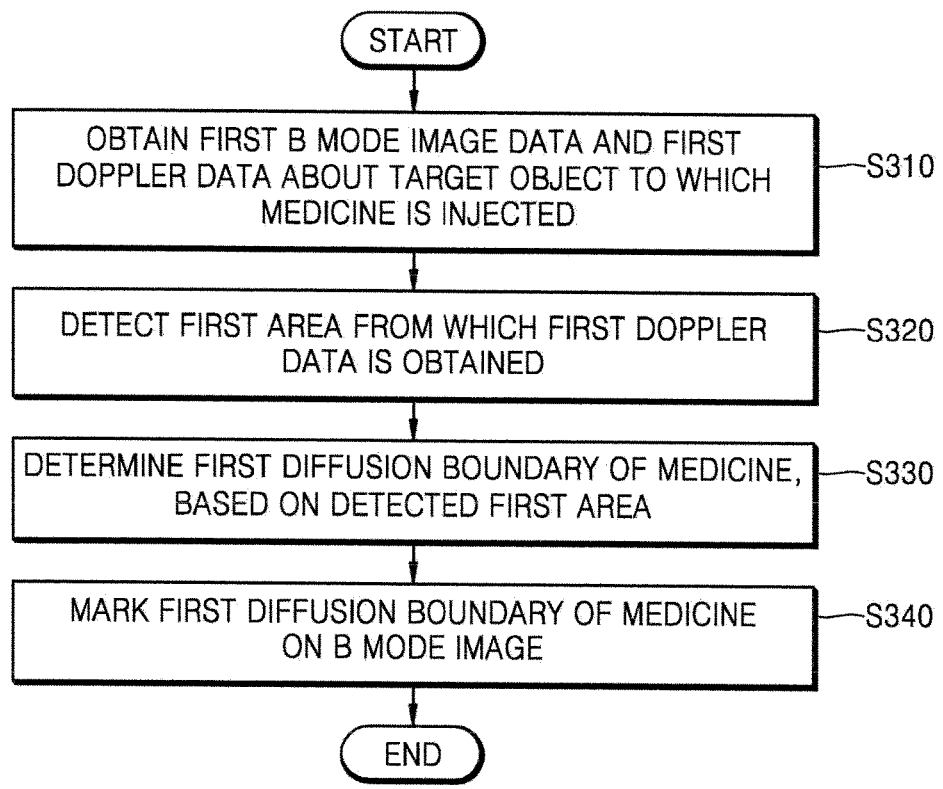
FIG. 3 is a flowchart of a method of displaying a diffusion boundary of medicine, the method performed by the ultrasound apparatus, according to an embodiment of the present invention.

FIG. 3 is a flowchart of a method of displaying a diffusion boundary of medicine, the method performed by the ultrasound apparatus 1000, according to an embodiment of the present invention.

In operation S310, the ultrasound apparatus 1000 may obtain first B mode image data and first Doppler data about a target object to which the medicine is injected.

The first B mode image data may include brightness values in each pixel which corresponds to intensity of an ultrasound echo signal reflected from the target object. The first Doppler data may include, but is not limited to, frequency information about a Doppler signal obtained from the target object to which the medicine is injected, intensity information about the Doppler signal, diffusion speed information about the medicine, and information about a movement direction of the medicine.

Throughout the specification, Doppler data may include at least one of color Doppler image data and power Doppler image data. A color Doppler image indicates a color spectrum image of information about a direction and speed of the medicine, and the color Doppler image data may include color values that correspond to movement speed or a movement direction of the medicine. For example, when diffusion speed of the medicine is low, the color Doppler image data may include a value of a bright color, and when the diffusion speed of the medicine is high, the color Doppler image data may include a value of a dim color. Also, when a diffusion direction of the medicine is close to a probe, the color Doppler image data may include a value of a red-based color, and when the diffusion direction of the medicine is distant from the probe, the color Doppler image data may include a value of a blue-based color.

In the present embodiment, the power Doppler image data may include data about an area where the medicine diffuses, regardless of the diffusion direction of the medicine. A power Doppler image is obtained by imaging intensity of the Doppler signal, and is characterized that it is less sensitive to an incident degree and thus does not have an aliasing signal, and that it has less image attenuation against noise. Also, the power Doppler image may sensitively show a small blood vessel and a slow blood flow. Thus, according to the present embodiment, the ultrasound apparatus 1000 may detect medicine that slowly diffuses, by using the power Doppler image data.

The ultrasound apparatus 1000 may directly generate first B mode image data and first Doppler data or may receive them from an outer source. For example, the ultrasound apparatus 1000 may transmit an ultrasound signal to the target object, may receive an ultrasound echo signal reflected from the target object, and thus may generate the first B mode image data and the first Doppler data. Also, the ultrasound apparatus 1000 may receive the first B mode image data and the first Doppler data from an external server or an external device.

In operation S320, the ultrasound apparatus 1000 may detect a first area of the target object from which the first Doppler data is obtained. For example, the ultrasound apparatus 1000 may detect an area where the Doppler signal is generated due to the diffusion of the medicine. In the present embodiment, the first area from which the first Doppler data is obtained may indicate an area of the target object in which the medicine diffuses.

In the present embodiment, when a speed value included in the first Doppler data is equal to or greater than a threshold value, the ultrasound apparatus 1000 may detect the first area from which the first Doppler data is obtained. For example, the ultrasound apparatus 1000 may detect an area where the medicine diffuses, only when the diffusion speed of the medicine is equal to or greater than the threshold value. When the diffusion speed of the medicine is less than the threshold value, it means that the medicine has not been injected or does not diffuse, so that detecting the first area may be meaningless.

In operation S330, the ultrasound apparatus 1000 may determine a first diffusion boundary of the medicine, based on the first area from which the first Doppler data is obtained. For example, the ultrasound apparatus 1000 may determine an outside area of the first area from which the first Doppler data is obtained, as the first diffusion boundary of the medicine.

The ultrasound apparatus 1000 may detect a partial area of the first area where a speed value included in the first Doppler data is equal to or greater than the threshold value. Then, the ultrasound apparatus 1000 may determine an outside area of the partial area, as the first diffusion boundary of the medicine. In this case, the ultrasound apparatus 1000 may filter Doppler data that is generated due to motion of a tissue which is regardless of the diffusion of the medicine, and thus may correctly detect the diffusion boundary of the medicine.

In operation S340, the ultrasound apparatus 1000 may mark the first diffusion boundary of the medicine on a B mode image that is generated by using the first B mode image data.

The ultrasound apparatus 1000 may mark the first diffusion boundary of the medicine by using a line having a preset form. For example, the ultrasound apparatus 1000 may mark the first diffusion boundary of the medicine by using a solid line, a dotted line, a one dot-and-dash line, a two dots-and-dash line, etc., or by using a line with various colors such as red, blue, green, yellow, etc.

The ultrasound apparatus 1000 may translucently display the first Doppler image that is generated based on the first Doppler data. Throughout the specification, the term 'translucent' may mean that transparency is greater than 0% and less than 100%. For example, the ultrasound apparatus 1000 may mark the first diffusion boundary on the B mode image by translucently displaying the first Doppler image.

Here, according to the present embodiment, the ultrasound apparatus 1000 may adjust transparency of the first Doppler image. For example, the ultrasound apparatus 1000 may set the transparency of the first Doppler image as a value that is greater than 0% and less than 100%. The ultrasound apparatus 1000 may receive an input of user selection with respect to the transparency via a particular graphical user interface (GUI).

Also, the ultrasound apparatus 1000 may transparently display the first Doppler image on the B mode image, and may mark the first diffusion boundary by using a solid line, a dotted line, a one dot-and-dash line, etc. For example, the ultrasound apparatus 1000 may adjust the transparency of the first Doppler image as 100%, according to a user input or a system setting. Alternatively, the ultrasound apparatus 1000 may not display the first Doppler image on the B mode image.

The ultrasound apparatus 1000 may provide quantified numerical data about a diffusion range of the medicine. For example, the ultrasound apparatus 1000 may display at least one of a diameter, a circumference, an area, and a volume with respect to the diffusion range of the medicine on the B mode image.

The ultrasound apparatus 1000 may provide comparison data obtained by comparing an estimated diffusion range of the medicine with an actual diffusion range of the medicine. For example, the ultrasound apparatus 1000 may estimate the diffusion range of the medicine, based on at least one of information about an interest position to which the medicine is injected, and information about an injection amount of the medicine. Also, the ultrasound apparatus 1000 may obtain information about the actual diffusion range (e.g., the first area from which the first Doppler data is obtained) of the medicine. Then, the ultrasound apparatus 1000 may compare the estimated diffusion range of the medicine with the actual diffusion range of the medicine. For example, the ultrasound apparatus 1000 may compare the estimated diffusion range of the medicine with at least one of a diameter, a circumference, an area, and a volume with respect to the actual diffusion range of the medicine. Afterward, the ultrasound apparatus 1000 may mark a comparison result (e.g., an error rate) on the B mode image.

With reference to FIG. 4, an operation by which the ultrasound apparatus 1000 marks the first diffusion boundary of the medicine on the first B mode image will be described in detail.

Figure 4B:
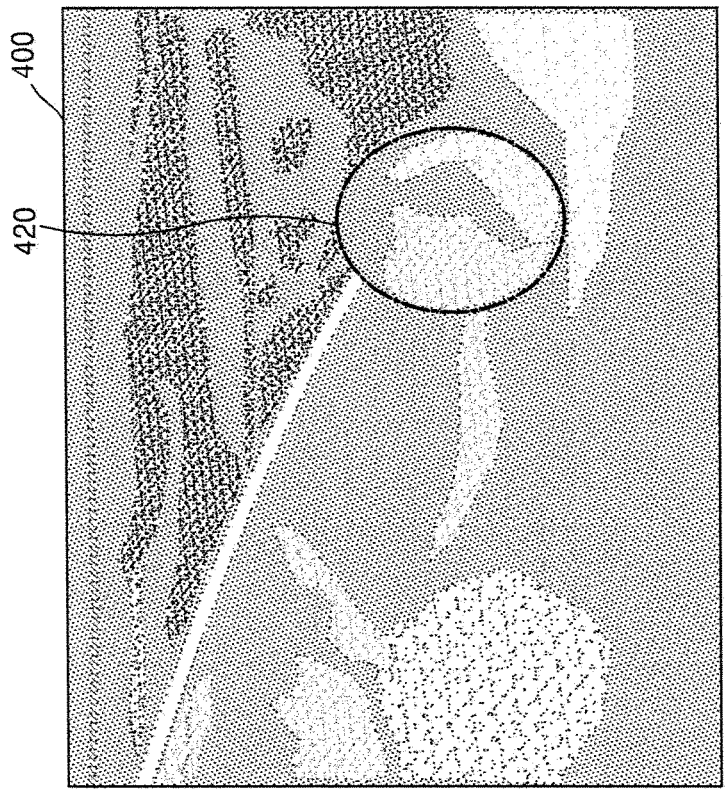
FIGS. 4A and 4B illustrate examples where the ultrasound apparatus marks a diffusion boundary of medicine by using Doppler data, according to an embodiment of the present invention.
Figure 4A:
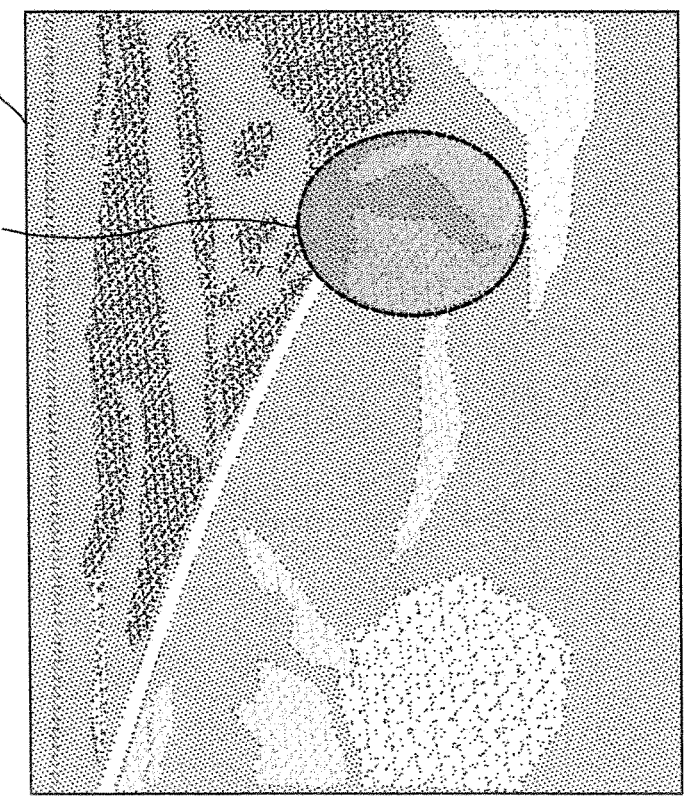

FIGS. 4A and 4B illustrate an example where the ultrasound apparatus 1000 marks a diffusion boundary of medicine by using Doppler data, according to an embodiment of the present invention.

As illustrated in FIG. 4A, the ultrasound apparatus 1000 may display a B mode image 400 of a target object to which the medicine is injected. Then, the ultrasound apparatus 1000 may mark the diffusion boundary of the medicine, which is determined based on the Doppler data, on the B mode image 400 by using a dotted line 410. Here, the ultrasound apparatus 1000 may translucently display a Doppler image that is generated based on the Doppler data.

When the Doppler image is translucently displayed, a structure behind the Doppler image is not blinded by the Doppler image, so that a user may check whether the medicine has been correctly injected into a target structure in the target object.

As illustrated in FIG. 4B, the ultrasound apparatus 1000 may mark the diffusion boundary of the medicine on the B mode image 400 by using a one dot-and-dash line 420, and may not display the Doppler image or may transparently display the Doppler image.

When the Doppler image is not displayed or is transparently displayed, the structure behind the Doppler image is not blinded by the Doppler image, so that the user may check whether the medicine has been correctly injected into the target structure in the target object.

In the present embodiment, the ultrasound apparatus 1000 may display information about a diffusion range of the medicine in the form of text. For example, the ultrasound apparatus 1000 may display information about an area or a circumference of a diffusion area of the medicine on a predetermined region of a screen.

Figure 5:
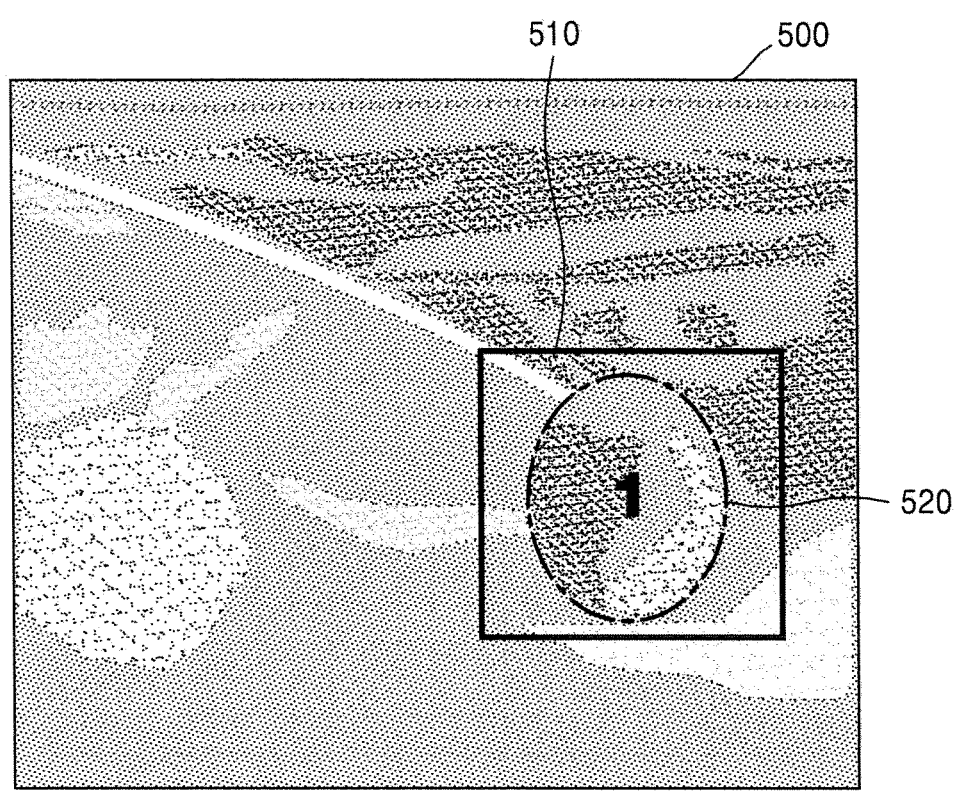
FIG. 5 illustrates an region of interest, according to an embodiment of the present invention.

FIG. 5 illustrates a region of interest 510, according to an embodiment of the present invention.

As illustrated in FIG. 5, when the region of interest 510 is set, the ultrasound apparatus 1000 may mark a diffusion boundary of medicine 520 in the region of interest 510.

In the present embodiment, the ultrasound apparatus 1000 may select at least one region of interest, based on a user input. For example, the ultrasound apparatus 1000 may receive a user input of selecting the region of interest 510 as an area of a B mode image 500 which includes a needle tip image.

The user input of selecting the region of interest 510 may vary. For example, the user input may be, but is not limited to, at least one of a key input, a touch input (e.g., a tap input, a double tap input, a drag & drop input, a flick input, a swipe input, etc.), a voice input, a motion input, and a multimodal input.

A shape of the region of interest 510 may vary. For example, the shape of the region of interest 510 may be, but is not limited to, circular, oval, quadrangular, free curve, etc.

The ultrasound apparatus 1000 may semi-automatically select the region of interest 510. For example, the ultrasound apparatus 1000 may receive an input of selecting a particular point from the user. The ultrasound apparatus 1000 may select the region of interest 510 having a predetermined size (e.g., 10 pixels or 5 cm$^2$) around the user-selected particular point. The predetermined size may be previously set by the user or the ultrasound apparatus 1000.

The ultrasound apparatus 1000 may change a position or a size of the region of interest 510, based on a user input.

When the region of interest 510 is set, the ultrasound apparatus 1000 may analyze Doppler data obtained from the region of interest 510, and thus may determine the diffusion boundary of medicine 520. In this case, the ultrasound apparatus 1000 analyzes only the Doppler data obtained from the region of interest 510, so that it is possible to decrease a time taken in detecting the diffusion boundary of medicine 520. Also, the ultrasound apparatus 1000 may mark the diffusion boundary of medicine 520 in the region of interest 510. Here, the ultrasound apparatus 1000 may translucently or transparently display the Doppler image.

Figure 6:
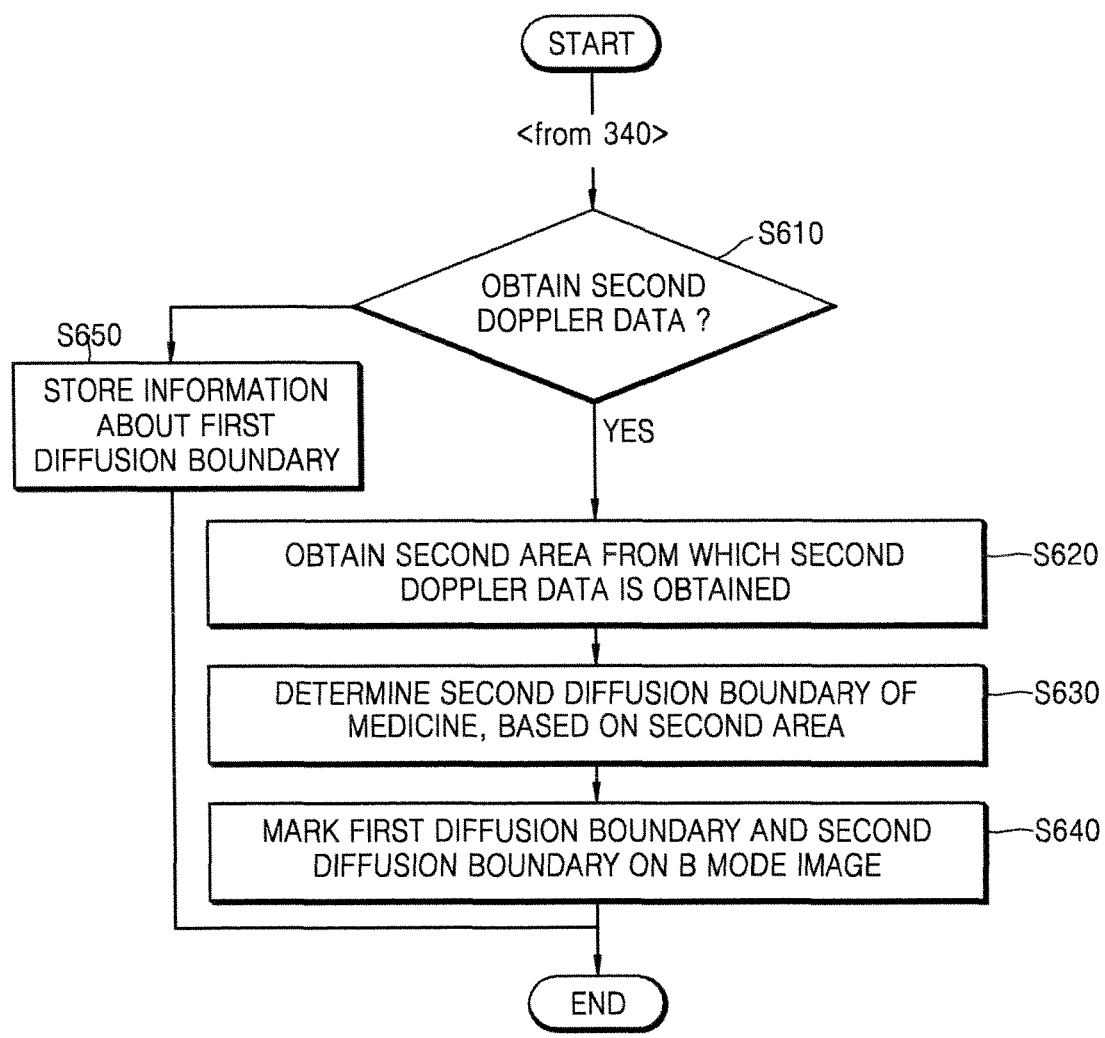
FIG. 6 is a flowchart of a method of marking a plurality of diffusion boundaries, the method performed by the ultrasound apparatus, according to an embodiment of the present invention.

FIG. 6 is a flowchart of a method of marking a plurality of diffusion boundaries, the method performed by the ultrasound apparatus 1000, according to an embodiment of the present invention.

In the present embodiment, medicine may be continuously injected into a target object for a predetermined time period via the needle 30. The ultrasound apparatus 1000 may determine a first diffusion boundary of the medicine by using first Doppler data about the target object to which the medicine is injected, and may mark the first diffusion boundary of the medicine on a B mode image. A procedure by which the ultrasound apparatus 1000 marks the first diffusion boundary of the medicine on the B mode image corresponds to operations S310 through S340 of FIG. 3, thus, detailed descriptions thereof are omitted here.

In operation S610, the ultrasound apparatus 1000 may obtain second Doppler data about the target object. The ultrasound apparatus 1000 may obtain the second Doppler data after the first Doppler data is obtained and then a preset time (e.g., 0.01 seconds) elapses. A period by which the ultrasound apparatus 1000 obtains the Doppler data may be changed by user's setting or the system.

In operation S620, the ultrasound apparatus 1000 may obtain a second area from which the second Doppler data is obtained. For example, as the medicine is continuously injected into the target object, the ultrasound apparatus 1000 may detect the second area from which the second Doppler data is obtained, which is different from the first area from which the first Doppler data is obtained.

In operation S630, the ultrasound apparatus 1000 may determine a second diffusion boundary of the medicine, based on the second area from which the second Doppler data is obtained. For example, the ultrasound apparatus 1000 may determine an outside area of the second area from which the second Doppler data is obtained, as the second diffusion boundary of the medicine.

In operation S640, the ultrasound apparatus 1000 may mark the first diffusion boundary of the medicine and the second diffusion boundary of the medicine on the B mode image. The ultrasound apparatus 1000 may mark each of the first diffusion boundary of the medicine and the second diffusion boundary of the medicine, by using a line having a preset form. For example, the ultrasound apparatus 1000 may mark the first diffusion boundary of the medicine and the second diffusion boundary of the medicine by using a dotted line. Alternatively, the ultrasound apparatus 1000 may mark the first diffusion boundary of the medicine by using a dotted line and may mark the second diffusion boundary of the medicine by using a one dot-and-dash line.

The ultrasound apparatus 1000 may translucently display a first Doppler image generated based on the first Doppler data and a second Doppler image generated based on the second Doppler data. Here, the ultrasound apparatus 1000 may adjust transparency of the first Doppler image or the second Doppler image. The transparency of the first Doppler image may be equal to or different from the transparency of the second Doppler image.

When the first Doppler image and the second Doppler image are power Doppler images, the ultrasound apparatus 1000 may display the first Doppler image and the second Doppler image by using the same color or different colors.

In the present embodiment, the ultrasound apparatus 1000 may transparently display the first Doppler image and the second Doppler image or may not display the first Doppler image and the second Doppler image. In this case, only the first diffusion boundary and the second diffusion boundary are marked on the B mode image, so that a user may check whether the medicine is correctly injected into a target structure in the target object.

When a region of interest area is set in the B mode image, the ultrasound apparatus 1000 may mark the first diffusion boundary of the medicine and the second diffusion boundary of the medicine in the region of interest.

In operation S650, when the second Doppler data is not obtained, the ultrasound apparatus 1000 may store information about the first diffusion boundary. For example, when the medicine that is injected into the target object no longer diffuses, a Doppler signal may not be further generated. In this case, the ultrasound apparatus 1000 may determine the first diffusion boundary of the medicine as a final diffusion boundary, and may automatically store the information about the first diffusion boundary. That is, when Doppler data about the target object is no longer obtained, the ultrasound apparatus 1000 may store and manage the information about the first diffusion boundary which was previously determined.

Figure 7:
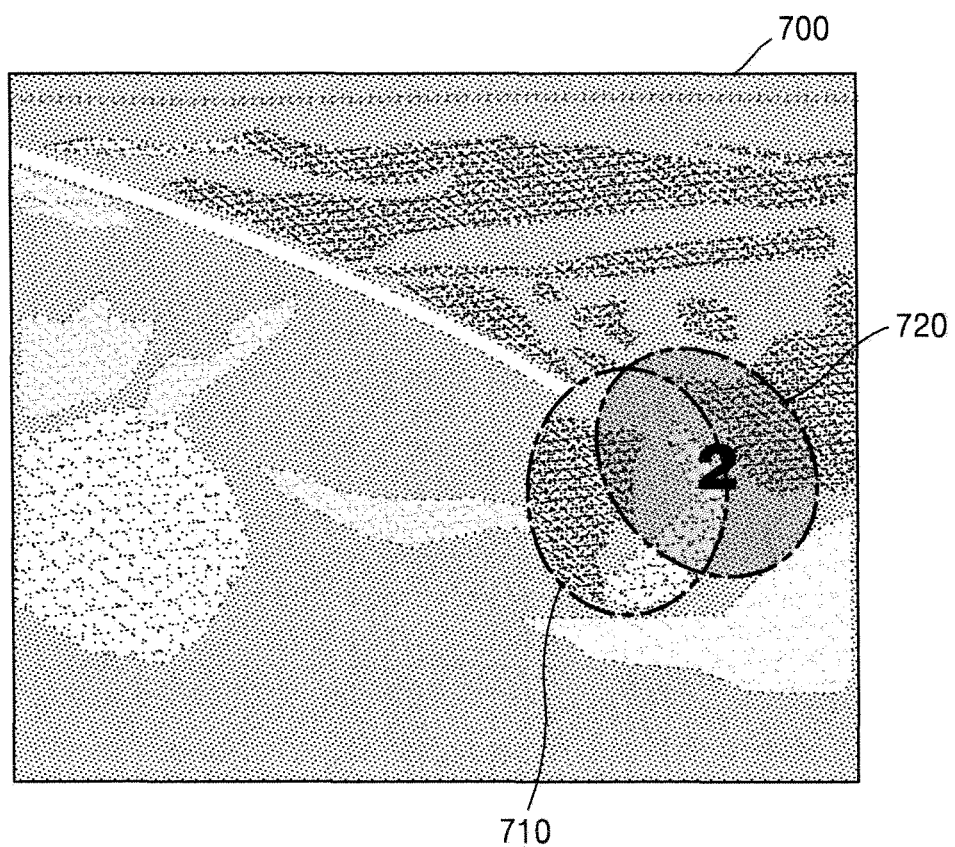
FIG. 7 illustrates an ultrasound image whereon a first diffusion boundary of medicine and a second diffusion boundary of the medicine are marked.

FIG. 7 illustrates an ultrasound image whereon a first diffusion boundary of medicine and a second diffusion boundary of the medicine are marked. FIG. 7 corresponds to an example where the medicine is continuously injected into a target object for a predetermined time period via the needle 30.

As illustrated in FIG. 7, the ultrasound apparatus 1000 may mark a first diffusion boundary 710 of the medicine on a B mode image 700 about the target object to which the medicine is injected. After an elapse of a predetermined time, the ultrasound apparatus 1000 may mark a second diffusion boundary 720 of the medicine on the B mode image 700.

By doing so, a user may recognize in real-time a change in a diffusion boundary of the medicine that is continuously injected. Thus, in the present embodiment, if the medicine has been correctly injected to a target structure in the target object, the user no longer injects the medicine, so that an amount of the medicine injected into the target object may be reduced.

In the example of FIG. 7, a first Doppler image is transparently displayed whereas a second Doppler image is translucently displayed, but one or more embodiments of the present invention are not limited thereto. For example, the ultrasound apparatus 1000 may transparently or translucently display all of the first Doppler image and the second Doppler image.

In the example of FIG. 7, the ultrasound apparatus 1000 displays the first and second diffusion boundaries 710 and 720 on the B mode image 700, but one or more embodiments of the present invention are not limited thereto. For example, the ultrasound apparatus 1000 may display at least three diffusion boundaries on the B mode image 700.

Figure 8:
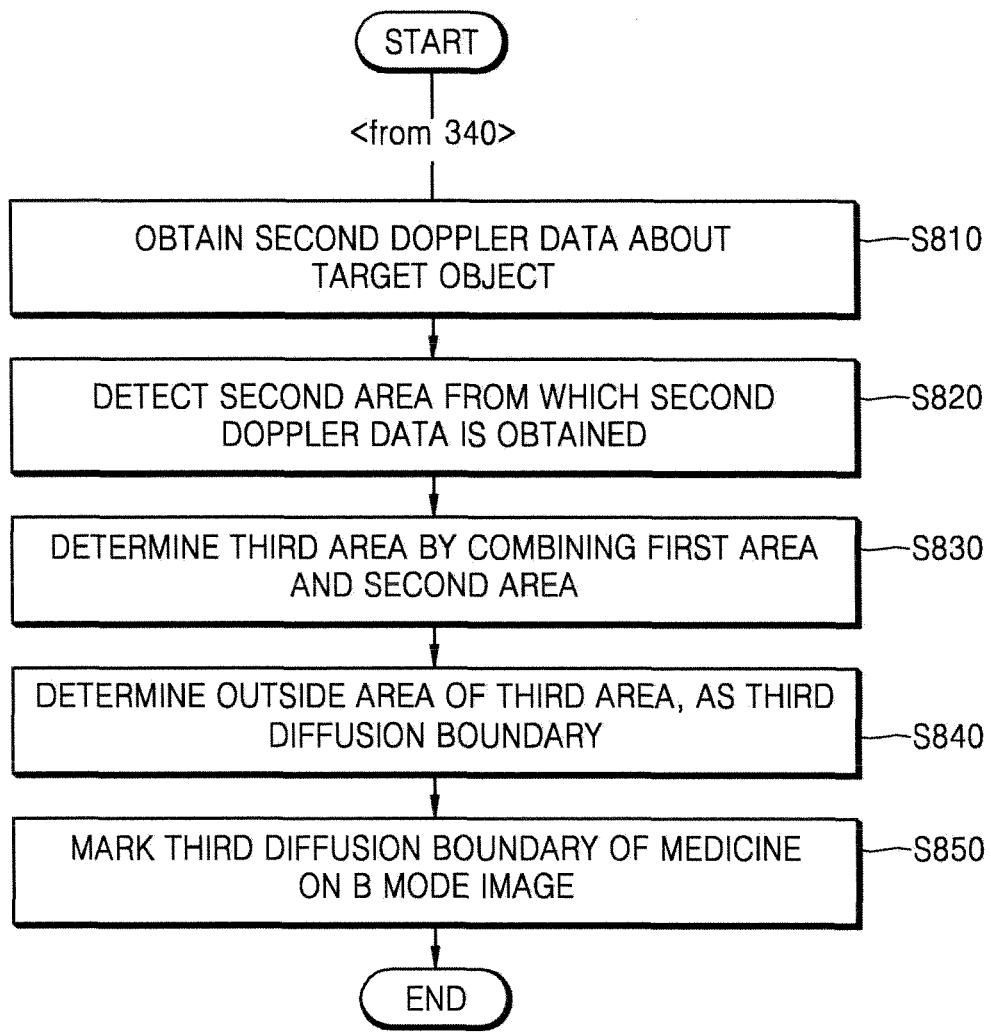
FIG. 8 is a flowchart of a method of sequentially extending a diffusion boundary of medicine and displaying the diffusion boundary, the method performed by the ultrasound apparatus, according to an embodiment of the present invention.

FIG. 8 is a flowchart of a method of sequentially extending a diffusion boundary of medicine and displaying the diffusion boundary, the method performed by the ultrasound apparatus 1000, according to an embodiment of the present invention.

In the present embodiment, medicine may be continuously injected into a target object for a predetermined time period via the needle 30. The ultrasound apparatus 1000 may determine a first diffusion boundary of the medicine by using first Doppler data about the target object to which the medicine is injected, and may mark the first diffusion boundary of the medicine on a B mode image. A procedure by which the ultrasound apparatus 1000 marks the first diffusion boundary of the medicine on the B mode image corresponds to operations S310 through S340 of FIG. 3, thus, detailed descriptions thereof are omitted here.

In operation S810, the ultrasound apparatus 1000 may obtain second Doppler data about the target object. The ultrasound apparatus 1000 may obtain the second Doppler data after the first Doppler data is obtained and then a preset time (e.g., 0.01 seconds) elapses.

In operation S820, the ultrasound apparatus 1000 may detect a second area from which the second Doppler data is obtained. Since operations S810 and S820 correspond to operations S610 and S620 of FIG. 6, detailed descriptions thereof are omitted here.

In operation S830, the ultrasound apparatus 1000 may determine a third area by combining the first area and the second area. Since the third area is determined by combining the first area from which the first Doppler data is obtained with the second area from which the second Doppler data is obtained, the third area may be larger than the first area.

In operation S840, the ultrasound apparatus 1000 may determine an outside area of the third area, as a third diffusion boundary.

In operation S850, the ultrasound apparatus 1000 may mark the third diffusion boundary of the medicine on the B mode image.

In the present embodiment, the ultrasound apparatus 1000 may mark the third diffusion boundary of the medicine by using a line having a preset form. For example, the ultrasound apparatus 1000 may mark the third diffusion boundary of the medicine by using a solid line, a dotted line, a one dot-and-dash line, a two dots-and-dash line, etc., or by using a line with various colors such as red, blue, green, yellow, etc.

The ultrasound apparatus 1000 may translucently display the first Doppler image generated based on the first Doppler data and the second Doppler image generated based on the second Doppler data. Here, the ultrasound apparatus 1000 may adjust transparency of the first Doppler image or the second Doppler image. The transparency of the first Doppler image may be equal to or different from the transparency of the second Doppler image.

When the first Doppler image and the second Doppler image are power Doppler images, the ultrasound apparatus 1000 may display the first Doppler image and the second Doppler image by using the same color or different colors.

The ultrasound apparatus 1000 may transparently display or may not display the first Doppler image and the second Doppler image. By doing so, only the third diffusion boundary is marked on the B mode image, so that the user may check whether the medicine has been correctly injected into a target structure in the target object.

Also, in the present embodiment, when a region of interest is set, the ultrasound apparatus 1000 may mark a third diffusion boundary of the medicine on the region of interest.

Figure 9A:
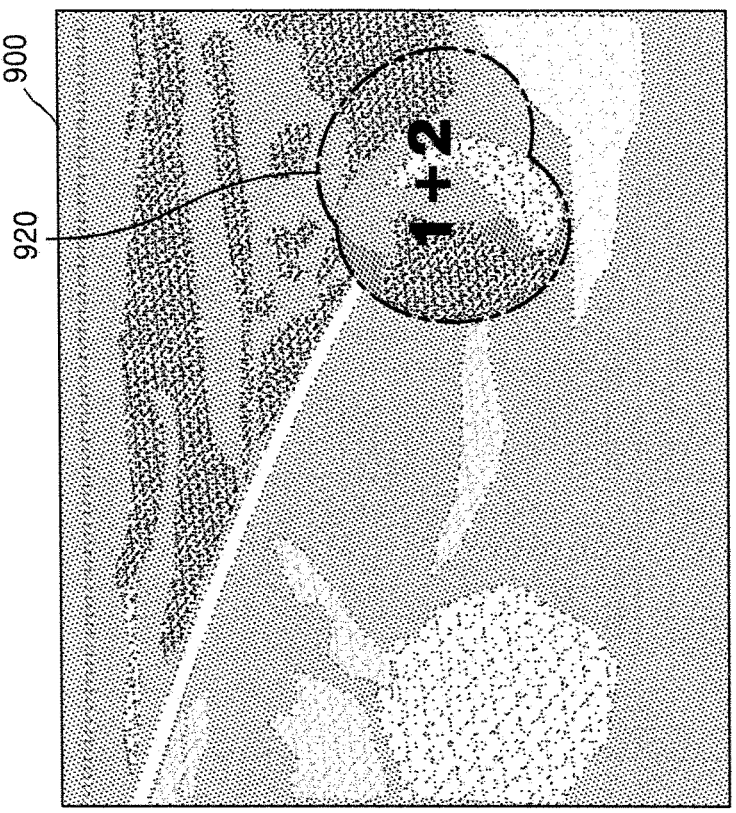
FIGS. 9A and 9B illustrate ultrasound images whereon an extended diffusion boundary is marked.
Figure 9B:
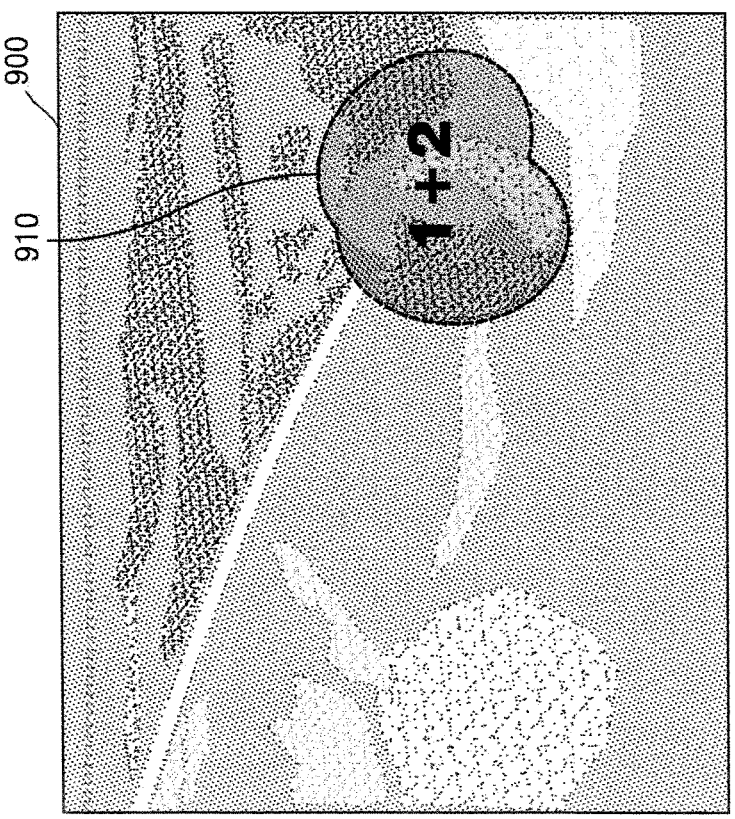

FIGS. 9A and 9B illustrate ultrasound images whereon an extended diffusion boundary is marked. FIGS. 9A and 9B correspond to examples where medicine is continuously injected into a target object for a predetermined time period via the needle 30.

As illustrated in FIG. 9A, the ultrasound apparatus 1000 may determine an outside area of a third area as a third diffusion boundary of the medicine on a B mode image 900 about the target object to which the medicine is injected, wherein the third area is determined by combining a first area from which first Doppler data is obtained with a second area from which second Doppler data is obtained. Then, the ultrasound apparatus 1000 may mark the third diffusion boundary by using a dotted line 910. By doing so, a user may recognize in real-time a change in a diffusion boundary of the medicine that is continuously injected.

The ultrasound apparatus 1000 may translucently display a first Doppler image generated based on the first Doppler data and a second Doppler image generated based on the second Doppler data. In this case, the user may recognize a structure behind the first Doppler image and the second Doppler image. Thus, if the medicine has been correctly injected to a target structure in the target object, the user no longer injects the medicine, so that an amount of the medicine injected into the target object may be reduced.

As illustrated in FIG. 9B, the ultrasound apparatus 1000 may mark the third diffusion boundary of the medicine on the B mode image 900 by using a one dot-and-dash line 920, and may not display the first Doppler image and the second Doppler image. When the first Doppler image and the second Doppler image are not displayed, a structure behind the first Doppler image and the second Doppler image are not blinded, so that the user may check whether the medicine has been correctly injected into the target structure in the target object.

FIG. 10 is a flowchart of a method of storing information about a diffusion boundary of medicine, the method performed by the ultrasound apparatus 1000, according to an embodiment of the present invention.

In the present embodiment, the ultrasound apparatus 1000 may determine a first diffusion boundary of the medicine by using first Doppler data about the target object to which the medicine is injected, and may mark the first diffusion boundary of the medicine on a B mode image that is generated based on first B mode image data. A procedure by which the ultrasound apparatus 1000 marks the first diffusion boundary of the medicine on the B mode image corresponds to operations S310 through S340 of FIG. 3, thus, detailed descriptions thereof are omitted here.

In operation S1010, the ultrasound apparatus 1000 may obtain second B mode image data about the target object. The ultrasound apparatus 1000 may obtain the second B mode image data after the first B mode image data is obtained and then a preset time (e.g., 0.01 seconds) elapses. A period by which the ultrasound apparatus 1000 obtains the B mode image data may be changed by user's setting or the system.

In operation S1020, the ultrasound apparatus 1000 may compare the first B mode image data with the second B mode image data.

In the present embodiment, as a result of the comparison, if similarity between the first B mode image data and the second B mode image data is equal to or greater than a preset value, the ultrasound apparatus 1000 may obtain second Doppler data. Then, the ultrasound apparatus 1000 may determine a second diffusion boundary or a third diffusion boundary by using the second Doppler data (refer to FIGS. 6 and 8).

For example, when the first B mode image data and the second B mode image data are equal to each other, the ultrasound apparatus 1000 may mark the first diffusion boundary, the second diffusion boundary, and the third diffusion boundary on the same B mode image. In this case, since the B mode image that is a background is hardly changed, a user may correctly check a diffusion range of the medicine.

In operation S1030, if the similarity between the first B mode image data and the second B mode image data is less than the preset value, the ultrasound apparatus 1000 may store information about the first diffusion boundary. For example, when the B mode image is changed due to movement of the probe 20 or motion of an examinee, the ultrasound apparatus 1000 may no longer detect a diffusion boundary. That is, since the B mode image that is a reference is changed, it is difficult for the ultrasound apparatus 1000 to correctly detect the diffusion boundary. Thus, the ultrasound apparatus 1000 may automatically store, in a memory, and manage the information about the first diffusion boundary which was previously determined.

Figure 11:
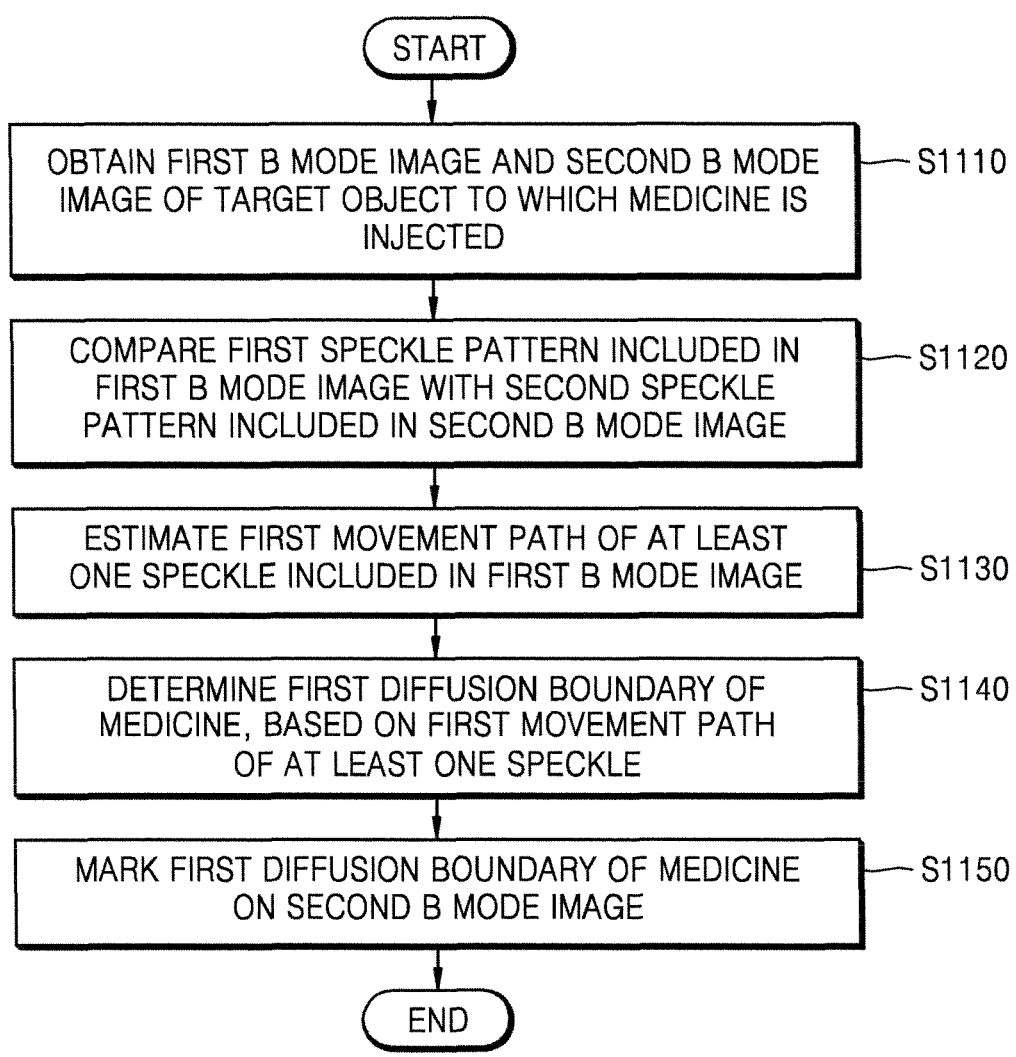
FIG. 11 is a flowchart of a method of marking a diffusion boundary of medicine by using a speckle tracking algorithm, the method performed by the ultrasound apparatus, according to an embodiment of the present invention.

FIG. 11 is a flowchart of a method of marking a diffusion boundary of medicine by using a speckle tracking algorithm, the method performed by the ultrasound apparatus 1000, according to an embodiment of the present invention.

In operation S1110, the ultrasound apparatus 1000 may obtain a first B mode image and a second B mode image of a target object to which the medicine is injected.

In the present embodiment, the ultrasound apparatus 1000 may obtain the second B mode image after the first B mode image is obtained and then a preset time (e.g., 0.01 seconds) elapses. Thus, compared to the time when the first B mode image was obtained, when the second B mode image is obtained, the medicine may have further diffused in the target object.

In the present embodiment, a period by which the ultrasound apparatus 1000 obtains a B mode image may be changed by user's setting or the system.

The ultrasound apparatus 1000 may directly generate a first B mode image and/or a second B mode image or may receive them from an outer source. For example, the ultrasound apparatus 1000 may transmit an ultrasound signal to the target object, may receive an ultrasound echo signal reflected from the target object, and thus may generate the first B mode image or the second B mode image. Also, the ultrasound apparatus 1000 may receive the first B mode image or the second B mode image from an external server or an external device.

In operation S1120, the ultrasound apparatus 1000 may compare a first speckle pattern included in the first B mode image with a second speckle pattern included in the second B mode image.

For example, the ultrasound apparatus 1000 may obtain a correlation between the first speckle pattern included in the first B mode image and the second speckle pattern included in the second B mode image. Then, the ultrasound apparatus 1000 may recognize where speckles that are included in the first B mode image are located in the second B mode image, by using the correlation. The higher the correlation between the first speckle pattern and the second speckle pattern is, there is a high possibility that a part of the first B mode image which includes the first speckle pattern, and a part of the second B mode image which includes the second speckle pattern indicate a same part in the target object.

The ultrasound apparatus 1000 may receive an input of selecting a region of interest in the target object. For example, the ultrasound apparatus 1000 may receive a user input of selecting an area including a needle tip, as the region of interest.

In this case, the ultrasound apparatus 1000 may compare the first speckle pattern of the first B mode image which is included in the region of interest with the second speckle pattern of the second B mode image which is included in the region of interest. Here, since the ultrasound apparatus 1000 analyzes only speckle patterns included in the region of interest, it is possible to reduce a time taken to analyze a correlation between the speckle patterns.

The user input of selecting the region of interest may vary. For example, the user input may be, but is not limited to, at least one of a key input, a touch input (e.g., a tap input, a double tap input, a touch & drag input, a flick input, a swipe input, etc.), a voice input, a motion input, and a multimodal input.

Also, a shape of the region of interest may vary. For example, the shape of the region of interest may be, but is not limited to, circular, oval, quadrangular, free curve, etc.

In operation S1130, the ultrasound apparatus 1000 may estimate a first movement path of at least one speckle included in the first B mode image, based on a result of the comparison between the first speckle pattern and the second speckle pattern.

In general, when the medicine is injected into the target object, a volume of a tissue to which the medicine is injected may extend. Thus, speckles around the tissue to which the medicine is injected may move. Here, since the speckles included in the B mode image may move while the speckles maintain a predetermined pattern, the ultrasound apparatus 1000 may estimate a movement path of the speckles by comparing the first speckle pattern with the second speckle pattern. This will be described in detail with reference to FIG. 12.

In operation S1140, the ultrasound apparatus 1000 may determine a first diffusion boundary of the medicine, based on the first movement path of at least one speckle.

For example, the ultrasound apparatus 1000 may determine a first movement area including the first movement path of the at least one speckle. Then, the ultrasound apparatus 1000 may determine an outside area of the first movement area, as the first diffusion boundary of the medicine.

The ultrasound apparatus 1000 may determine whether the first movement area is equal to or greater than a preset area. When the first movement area is equal to or greater than the preset area (e.g., 10 pixels or 9 cm$^2$), the ultrasound apparatus 1000 may determine the outside area of the first movement area, as the first diffusion boundary. When the first movement area is less than the preset area, the ultrasound apparatus 1000 may not determine the outside area of the first movement area, as the first diffusion boundary. Since when the first movement area is less than the preset area, the medicine may not appropriately diffuse.

In operation S1150, the ultrasound apparatus 1000 may mark the first diffusion boundary of the medicine on the second B mode image.

The ultrasound apparatus 1000 may mark the first diffusion boundary of the medicine by using a line having a preset form. For example, the ultrasound apparatus 1000 may mark the first diffusion boundary of the medicine by using a solid line, a dotted line, a one dot-and-dash line, a two dots-and-dash line, etc., or by using a line with various colors such as red, blue, green, yellow, etc.

When the region of interest is set, the ultrasound apparatus 1000 may mark the first diffusion boundary of the medicine in the region of interest.

The ultrasound apparatus 1000 may translucently or transparently display a speckle tracking image that is generated based on the first movement path of the at least one speckle. For example, the ultrasound apparatus 1000 may mark the first diffusion boundary on the second B mode image by translucently displaying the speckle tracking image. Also, the ultrasound apparatus 1000 may transparently display the speckle tracking image on the second B mode image, and may mark the first diffusion boundary by using a solid line, a dotted line, a one dot-and-dash line, etc.

The speckle tracking image may be obtained by imaging a movement distance and a movement direction of at least one speckle by using an arrow or a color. For example, the ultrasound apparatus 1000 may express the movement direction of the at least one speckle by using a direction of the arrow, and may express the movement distance of the at least one speckle by using a length of the arrow. Alternatively, the ultrasound apparatus 1000 may express the movement direction of the at least one speckle by using a specific color, and may express the movement distance of the at least one speckle by using a brightness of the color. When the ultrasound apparatus 1000 displays the speckle tracking image by using the arrow or the color, it is difficult for the user to exactly recognize a structure behind the speckle tracking image.

However, according to the present embodiment, since the ultrasound apparatus 1000 translucently or transparently displays the speckle tracking image, the user may exactly recognize the structure behind the speckle tracking image. If the medicine has been correctly injected to a target structure in the target object, the user no longer injects the medicine, so that an amount of the medicine injected into the target object may be reduced.

The ultrasound apparatus 1000 may provide quantified numerical data about a diffusion range of the medicine. For example, the ultrasound apparatus 1000 may display at least one of a diameter, a circumference, an area, and a volume with respect to the diffusion range of the medicine on the second B mode image.

The ultrasound apparatus 1000 may provide comparison data obtained by comparing an estimated diffusion range of the medicine with an actual diffusion range of the medicine. For example, the ultrasound apparatus 1000 may compare the estimated diffusion range of the medicine with at least one of a diameter, a circumference, an area, and a volume with respect to the actual diffusion range of the medicine.

Afterward, the ultrasound apparatus 1000 may mark a comparison result (e.g., an error rate) on the second B mode image.

Figure 12:
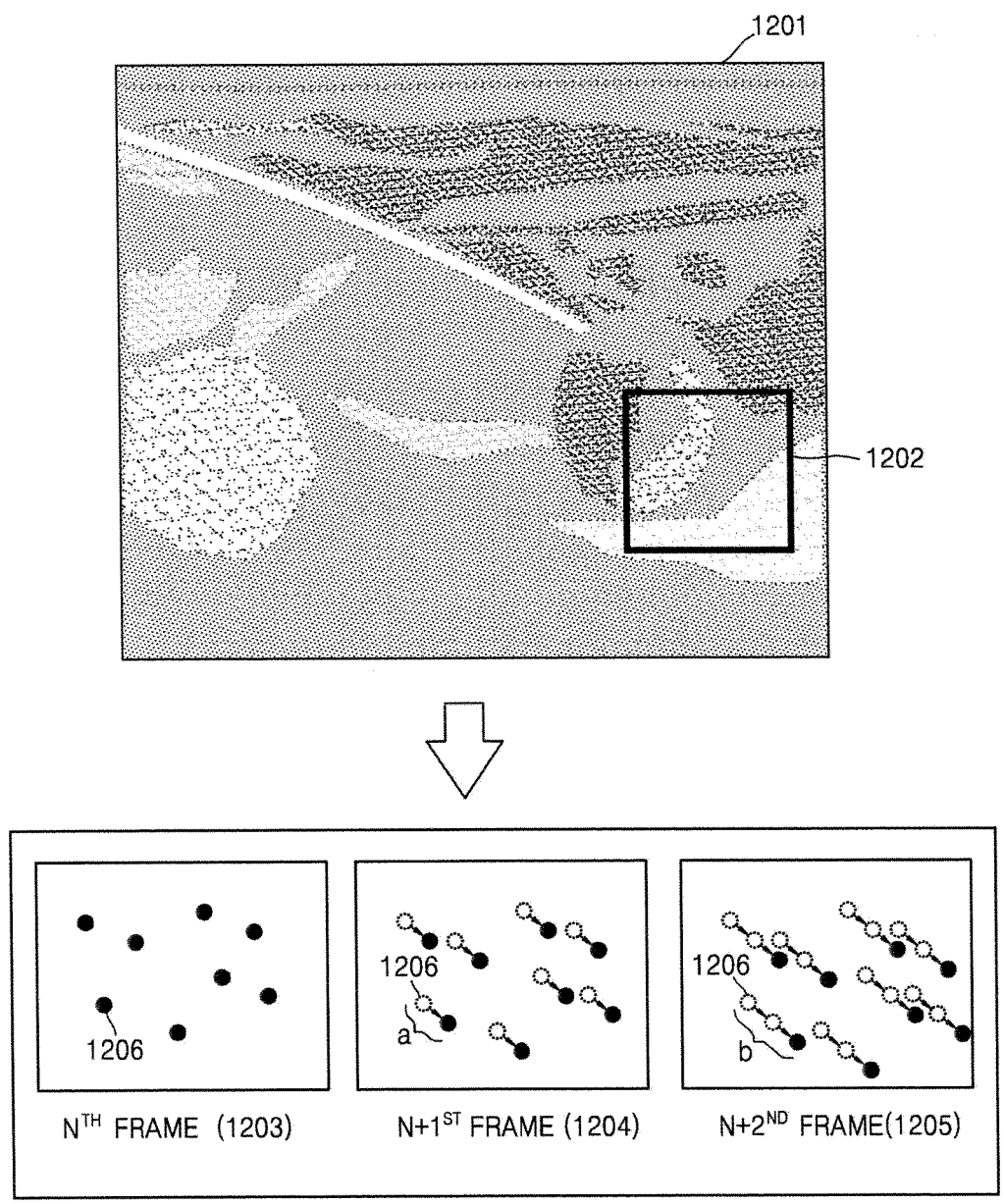
FIG. 12 illustrates a method of comparing speckle patterns included in ultrasound images, respectively, the method performed by the ultrasound apparatus, according to an embodiment of the present invention.

FIG. 12 illustrates a method of comparing speckle patterns included in ultrasound images, respectively, the method performed by the ultrasound apparatus 1000, according to an embodiment of the present invention.

In the present embodiment, medicine may be continuously injected into a target object for a predetermined time period via the needle 30. Here, the ultrasound apparatus 1000 may obtain a B mode image 1201 of the target object to which the medicine is injected. The ultrasound apparatus 1000 may set a region of interest 1202 based on a user input, and may compare speckle patterns between frames in the region of interest 1202.

For example, the ultrasound apparatus 1000 may sequentially obtain an $n^{th}$ frame 1203, an $n+1^{st}$ frame 1204, and an $n+2^{nd}$ frame 1205. The ultrasound apparatus 1000 may compare a speckle pattern of the $n^{th}$ frame 1203 with a speckle pattern of the $n+1^{st}$ frame 1204, and thus may obtain information indicating that a first speckle 1206 in the $n^{th}$ frame 1203 is moved in a lower right direction by an 'a' distance in the $n+1^{st}$ frame 1204.

Also, the ultrasound apparatus 1000 may further compare a speckle pattern of the $n+1^{st}$ frame 1204 with a speckle pattern of the $n+2^{nd}$ frame 1205, and thus may obtain information indicating that the first speckle 1206 in the $n^{th}$ frame 1203 is moved in a lower right direction by a 'b' distance in the $n+2^{nd}$ frame 1205. This is described with reference to FIG. 13.

Figure 13:
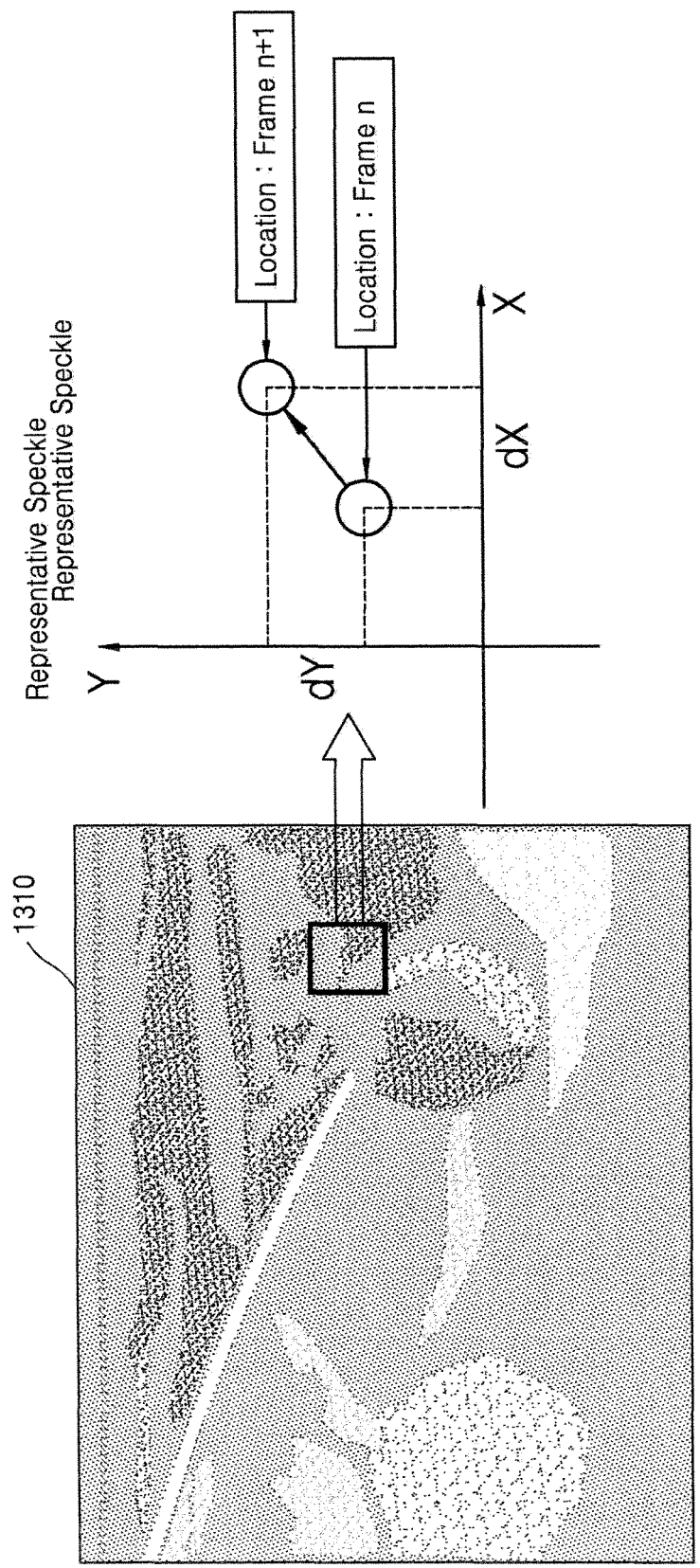
FIG. 13 illustrates an example where the ultrasound apparatus measures a movement distance of a speckle, according to an embodiment of the present invention.

FIG. 13 illustrates an example where the ultrasound apparatus 1000 measures a movement distance of a speckle, according to an embodiment of the present invention.

The ultrasound apparatus 1000 may compare a speckle pattern of an $n^{th}$ frame 1203 with a speckle pattern of an $n+1^{st}$ frame 1204, and thus may find a first speckle 1206 of the $n^{th}$ frame 1203 in the $n+1^{st}$ frame 1204.

Here, the ultrasound apparatus 1000 may compare a location of a first speckle 1206 in the $n^{th}$ frame 1203 with a location of the first speckle 1206 in the $n+1^{st}$ frame 1204, and thus may obtain information (e.g., a movement direction, a movement distance, etc.) about a movement path of the first speckle 1206.

Figure 14:
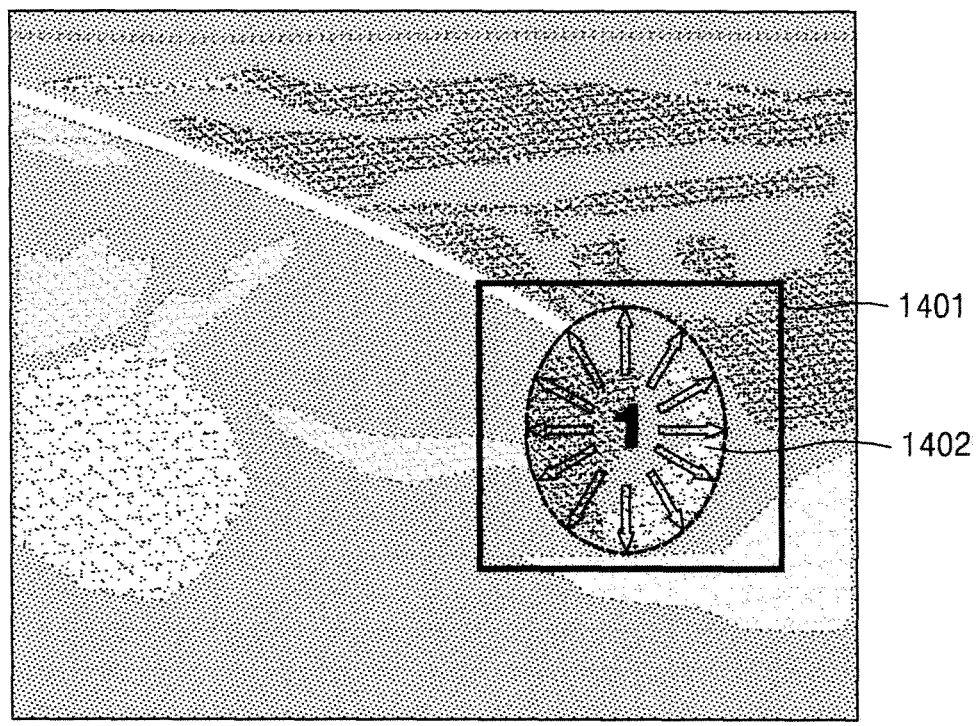
FIG. 14 illustrates an example of an operation by which the ultrasound apparatus determines a movement area including a movement path of a speckle, according to an embodiment of the present invention.

FIG. 14 illustrates an example of an operation by which the ultrasound apparatus 1000 determines a movement area including a movement path of a speckle, according to an embodiment of the present invention.

As illustrated in FIG. 14, the ultrasound apparatus 1000 may track locations of speckles included in a region of interest 1401 in a plurality of B mode images, and thus may estimate movement paths of the speckles. Then, the ultrasound apparatus 1000 may mark the movement paths of the speckles by using an arrow. However, when the movement paths of the speckles are marked by the arrow, a structure behind the arrow is blinded.

Figure 15:
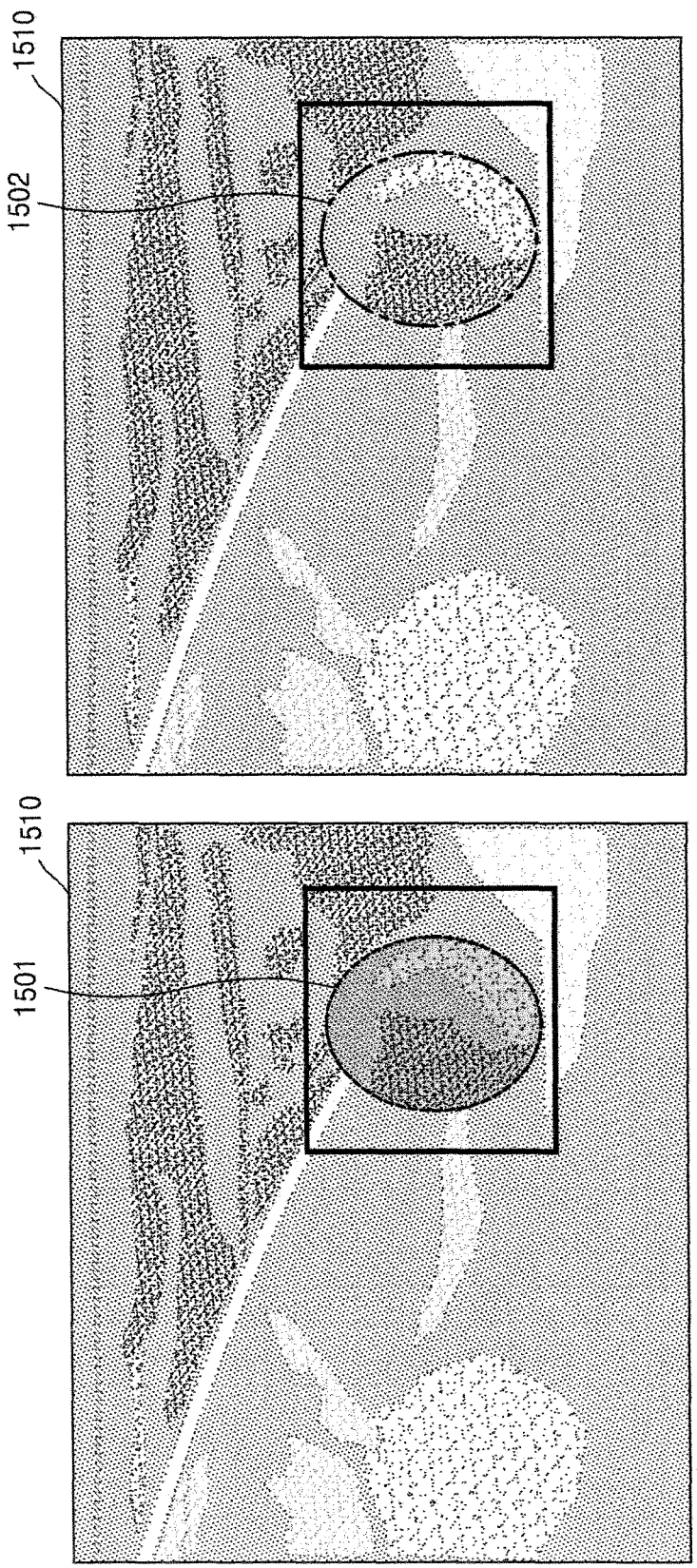
FIGS. 15A and 15B illustrate examples where the ultrasound apparatus marks a diffusion boundary of medicine by using a speckle tracking algorithm, according to an embodiment of the present invention.

Thus, the ultrasound apparatus 1000 may determine a first area 1402 including the movement paths of the speckles, and may mark an outside area of the first area 1402, as a first diffusion boundary of the medicine. This is described with reference to FIG. 15.

FIGS. 15A and 15B illustrate examples where the ultrasound apparatus 1000 marks a diffusion boundary of medicine by using a speckle tracking algorithm, according to an embodiment of the present invention.

As illustrated in FIG. 15A, the ultrasound apparatus 1000 may display a B mode image 1510 about a target object to which the medicine is injected. Then, the ultrasound apparatus 1000 may mark the diffusion boundary of the medicine, which is determined based on a movement path of at least one speckle, on the B mode image 1510 by using a dotted line 1501. Here, the ultrasound apparatus 1000 may translucently display a speckle tracking image, which is generated based on the movement path of the at least one speckle, on the B mode image 1510 by using a specific color.

When the speckle tracking image is translucently displayed, a structure behind the speckle tracking image is not blinded by the speckle tracking image, so that a user may check whether the medicine is correctly injected into a target structure in the target object.

As illustrated in FIG. 15B, the ultrasound apparatus 1000 may mark the diffusion boundary of the medicine on the B mode image 1510 by using a one dot-and-dash line 1502, and may not display or may transparently display the speckle tracking image.

When the speckle tracking image is not displayed or transparently displayed, the structure behind the speckle tracking image is not blinded by the speckle tracking image, so that the user may check whether the medicine is correctly injected into a target structure in the target object.

In the present embodiment, the ultrasound apparatus 1000 may display information about a diffusion range of the medicine in the form of text. For example, the ultrasound apparatus 1000 may display information about an area or a circumference of a diffusion area of the medicine on a predetermined region of a screen.

Figure 16:
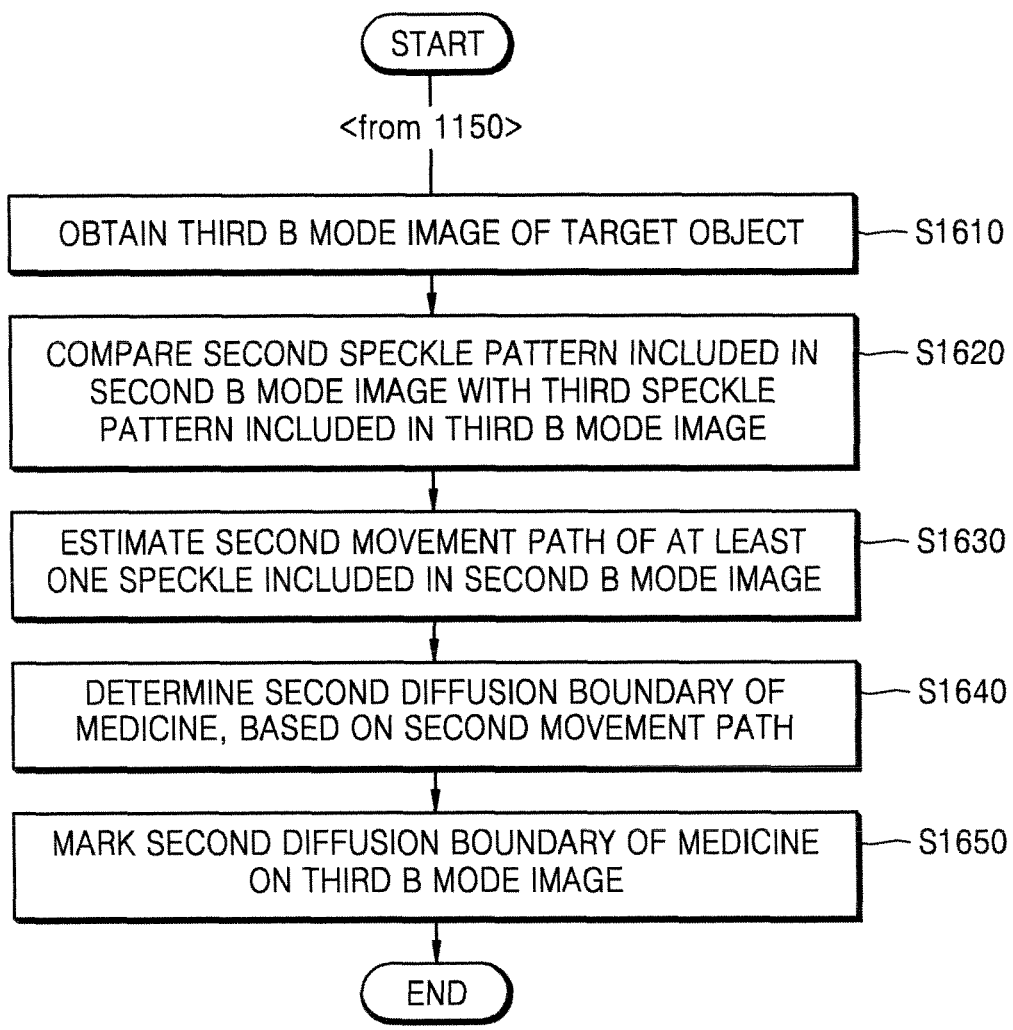
FIG. 16 is a flowchart of a method of continuously tracking at least one speckle and thus extending and marking a diffusion boundary of medicine, the method performed by the ultrasound apparatus, according to an embodiment of the present invention.

FIG. 16 is a flowchart of a method of continuously tracking at least one speckle and thus extending and marking a diffusion boundary of medicine, the method performed by the ultrasound apparatus 1000, according to an embodiment of the present invention.

In the present embodiment, the medicine may be continuously injected into a target object for a predetermined time period via the needle 30. Here, the ultrasound apparatus 1000 may determine a first diffusion boundary of the medicine by tracking a location of the at least one speckle in a first B mode image and a second B mode image of the target object to which the medicine is injected, and may mark the first diffusion boundary of the medicine on the second B mode image. A procedure by which the ultrasound apparatus 1000 marks the first diffusion boundary of the medicine on the second B mode image by using the speckle tracking algorithm corresponds to operations S1110 through S1150 of FIG. 11, and thus detailed descriptions thereof are omitted here.

In operation S1610, the ultrasound apparatus 1000 may obtain a third B mode image of the target object.

The ultrasound apparatus 1000 may obtain the third B mode image after a second B mode image is obtained and then a preset time (e.g., 0.01 seconds) elapses. Thus, compared to the time when the second B mode image was obtained, when the third B mode image is obtained, the medicine may have further diffused in the target object.

In the present embodiment, the ultrasound apparatus 1000 may directly generate the third B mode image or may receive the third B mode image from an external source.

In operation S1620, the ultrasound apparatus 1000 may compare a second speckle pattern included in the second B mode image with a third speckle pattern included in the third B mode image.

For example, the ultrasound apparatus 1000 may obtain a correlation between the second speckle pattern included in the second B mode image and the third speckle pattern included in the third B mode image. Then, the ultrasound apparatus 1000 may recognize where speckles that are included in the second B mode image are located in the third B mode image, by using the correlation. The higher the correlation between the second speckle pattern and the third speckle pattern is, there is a high possibility that a part of the second B mode image which includes the second speckle pattern, and a part of the third B mode image which includes the third speckle pattern indicate a same part in the target object.

In operation S1630, the ultrasound apparatus 1000 may estimate a second movement path of the at least one speckle included in the second B mode image, based on a result of the comparison between the second speckle pattern and the third speckle pattern.

For example, since speckles around a tissue to which the medicine has been injected move while the speckles maintain a predetermined pattern, the ultrasound apparatus 1000 may compare the second speckle pattern and the third speckle pattern and thus may estimate movement paths of the speckles around the tissue to which the medicine has been injected.

In operation S1640, the ultrasound apparatus 1000 may determine a second diffusion boundary of the medicine, based on the second movement path of the at least one speckle.

For example, the ultrasound apparatus 1000 may determine a second movement area including the second movement path of the at least one speckle. Then, the ultrasound apparatus 1000 may determine an outside area of the second movement area, as the second diffusion boundary of the medicine.

In the present embodiment, when a movement distance of the at least one speckle included in the second B mode image is less than a threshold value (or, when a difference between a second area and a first area is less than the threshold value), the ultrasound apparatus 1000 may determine the first diffusion boundary as a final diffusion boundary of the medicine, and may automatically store information about the first diffusion boundary. For example, when the speckles included in the B mode image no longer move, the ultrasound apparatus 1000 may determine that the diffusion of the medicine stops, and thus may store and manage the information about the first diffusion boundary which was previously determined.

In operation S1650, the ultrasound apparatus 1000 may mark the second diffusion boundary of the medicine on the third B mode image. For example, the ultrasound apparatus 1000 may mark the second diffusion boundary of the medicine by using a line with a preset form or a preset color.

The ultrasound apparatus 1000 may translucently display a speckle tracking image that is generated based on at least one of the first movement path and the second movement path of the at least one speckle. Here, the ultrasound apparatus 1000 may display a region within the first diffusion boundary, and a region between the first diffusion boundary and the second diffusion boundary in the speckle tracking image, by using different colors, different brightness levels, or different chroma levels.

The ultrasound apparatus 1000 may transparently display or may not display the speckle tracking image that is generated based on at least one of the first movement path and the second movement path of the at least one speckle.

The ultrasound apparatus 1000 may mark only the second diffusion boundary of the medicine on the third B mode image, or may mark the second diffusion boundary of the medicine and the first diffusion boundary of the medicine on the third B mode image.

As a result of the comparison between the second B mode image and the third B mode image, when similarity between the second B mode image and the third B mode image is less than a preset value, the ultrasound apparatus 1000 may store the information about the first diffusion boundary.

For example, when a difference between the second B mode image and the third B mode image is great due to movement of the probe 20 or motion of an examinee, the ultrasound apparatus 1000 may not be able to detect a diffusion boundary of the medicine by using the speckle tracking algorithm. Thus, the ultrasound apparatus 1000 may automatically store, in a memory, and manage the information about the first diffusion boundary which was previously determined.

Figure 17B:
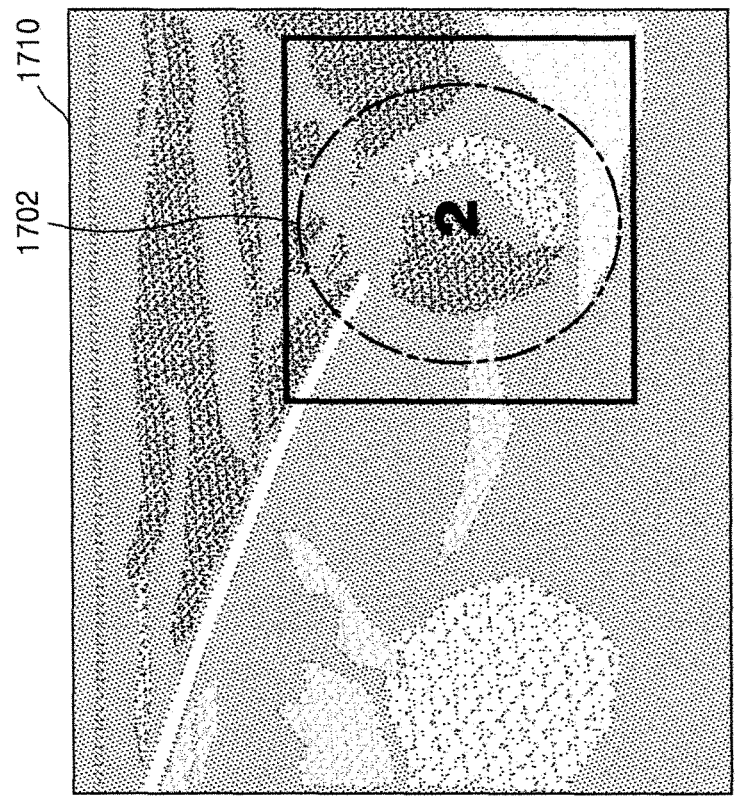
FIGS. 17A and 17B illustrate examples of an ultrasound image whereon an extended diffusion boundary is marked.
Figure 17A:
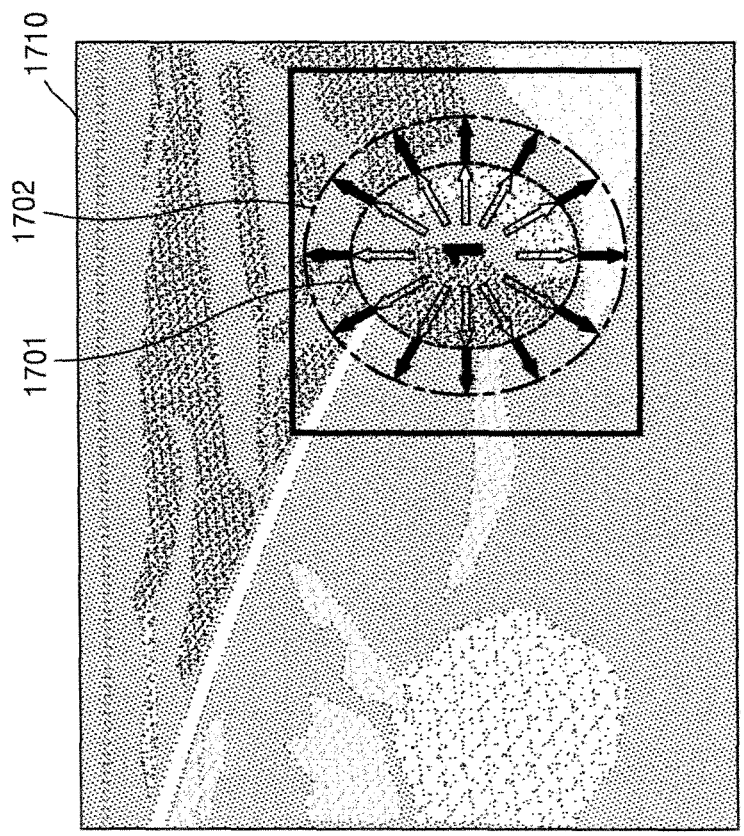

FIGS. 17A and 17B illustrate examples of an ultrasound image whereon an extended diffusion boundary is marked.

As illustrated in FIG. 17A, the ultrasound apparatus 1000 may mark a first diffusion boundary 1701 and a second diffusion boundary 1702 on a B mode image 1710 of a target object to which medicine is injected, by using a line. The ultrasound apparatus 1000 may mark the first diffusion boundary 1701 by using a dotted line, and may mark the second diffusion boundary 1702 by using a one dot-and-dash line. By doing so, a user may recognize in real-time a change in a diffusion boundary of the medicine that is continuously injected.

Also, the ultrasound apparatus 1000 may translucently display a speckle tracking image that indicates a movement path of a speckle. In this case, the user may check a structure behind the speckle tracking image. Thus, if the medicine has been correctly injected to a target structure in the target object, the user no longer injects the medicine, so that an amount of the medicine injected into the target object may be reduced.

As illustrated in FIG. 17B, the ultrasound apparatus 1000 may mark only the second diffusion boundary 1702 of the medicine on the B mode image 1710 by using a one dot-and-dash line, and may not display the speckle tracking image. When the speckle tracking image is not displayed, the structure behind the speckle tracking image is not blinded, so that the user may check whether the medicine is correctly injected into the target structure in the target object.

Figure 18:
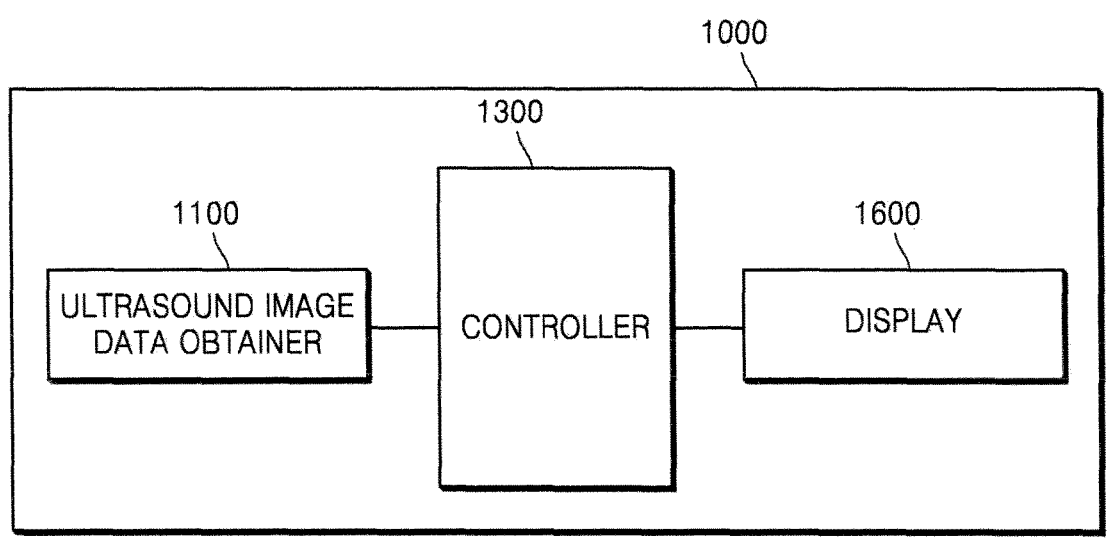
FIGS. 18 and 19 are block diagrams illustrating structures of the ultrasound apparatus, according to embodiments of the present invention.
Figure 19:
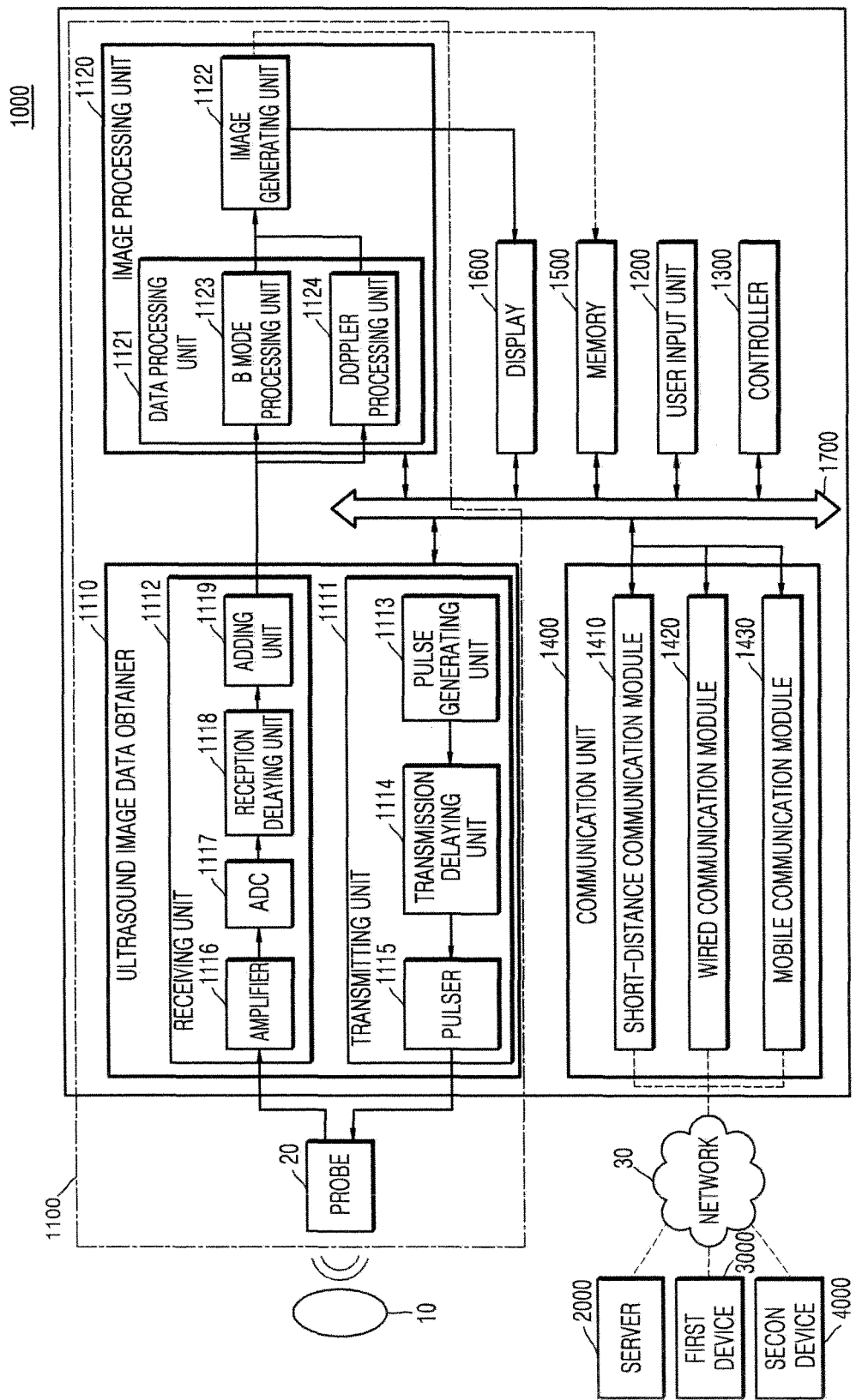

FIGS. 18 and 19 are block diagrams illustrating structures of the ultrasound apparatus 1000, according to embodiments of the present invention.

As illustrated in FIG. 18, the ultrasound apparatus 1000 may include an ultrasound image data obtainer 1100, a controller 1300, and a display 1600. However, not all elements shown in FIG. 18 are necessary elements. That is, the ultrasound apparatus 1000 may be embodied with more or less elements than the elements shown in FIG. 18. For example, as illustrated in FIG. 19, the ultrasound apparatus 1000 may further include a user input unit 1200, a communication unit 1400, and a memory 1500, in addition to the ultrasound image data obtainer 1100, the controller 1300, and the display 1600. The elements may be connected to each other via a bus 1700.

Hereinafter, the aforementioned elements are described.

The ultrasound image data obtainer 1100 may obtain ultrasound image data about a target object 10. In the present embodiment, the ultrasound image data may be 2D ultrasound image data or 3D ultrasound image data about the target object 10.

The ultrasound image data obtainer 1100 may include the probe 20, an ultrasound transmitting and receiving unit 1110, and an image processing unit 1120.

The probe 20 transmits an ultrasound signal to the target object 10 in response to a driving signal supplied from the ultrasound transmitting and receiving unit 1110, and receives an ultrasound echo signal reflected from the target object 10. The probe 20 includes a plurality of transducers that vibrate in response to a delivered electrical signal and thus generate ultrasound that is an acoustic energy. Also, the probe 20 may be connected to a body of the ultrasound apparatus 1000 in a wired or wireless manner, and the ultrasound apparatus 1000 may include a plurality of the probes 20 in one or more embodiments. In the present embodiment, the probe 20 may include at least one of 1D, 1.5D, 2D, and 3D probes.

The transmitting unit 1111 applies a driving signal to the probe 20, and includes a pulse generating unit 1113, a transmission delaying unit 1114, and a pulser 1115. The pulse generating unit 1113 generates pulses for generating transmission ultrasound according to a pulse repetition frequency (PRF), and the transmission delaying unit 1114 applies a delay time to the pulses so as to determine transmission directionality. The pulses to which the delay time is applied correspond to piezoelectric vibrators, respectively, which are included in the probe 20. The pulser 1115 applies the driving signal (or a driving pulse) to the probe 20 at a timing that corresponds to each of the pulses to which the delay time is applied.

A receiving unit 1112 may generate ultrasound data by processing the ultrasound echo signal from the probe 20, and may include an amplifier 1116, an analog-to-digital converter (ADC) 1117, a reception delaying unit 1118, and an adding unit 1119. The amplifier 1116 amplifies the ultrasound echo signal for each channel, and the ADC 1117 performs analog-to-digital conversion on the amplified ultrasound echo signal. The reception delaying unit 1118 applies a delay time to the digitally converted ultrasound echo signal so as to determine reception directionality, and the adding unit 1119 generates ultrasound image data by adding a plurality of the ultrasound echo signals that are processed by the reception delaying unit 1118.

The image processing unit 1120 generates an ultrasound image via a scan conversion process with respect to the ultrasound image data that is generated by the ultrasound transmitting and receiving unit 1110. The ultrasound image may include not only a gray scale image obtained by scanning the target object 10 during an amplitude mode (A mode), a brightness mode (B mode) or a motion mode (M mode) but also may include a Doppler image that expresses motion of the target object 10 by using a Doppler effect. The Doppler image may include a blood flow Doppler image (also referred as a color Doppler image) indicating a blood flow, a tissue Doppler image indicating movement of a tissue, a spectral Doppler image indicating a movement speed of the target object 10 by using a waveform, etc.

A B mode processing unit 1123 in a data processing unit 1121 extracts a B mode component from the ultrasound image data and thus processes the B mode component. The image generating unit 1122 may generate a B mode image based on the B mode component extracted by the B mode processing unit 1123, and intensity of a signal may be expressed as brightness in the B mode image. The image generating unit 1122 may sequentially generate a plurality of B mode images. For example, the image generating unit 1122 may generate a first B mode image and a second B mode image.

Similarly, a Doppler processing unit 1124 in the data processing unit 1121 may extract a Doppler component from the ultrasound image data, and may generate, based on the extracted Doppler component, a Doppler image that expresses the motion of the target object 10 by using a color or a waveform.

The image generating unit 1122 may generate a 3D ultrasound image via a volume rendering process on volume data, or may generate an elastic image by imaging deformation of the target object 10 due to a pressure applied thereto. Also, the image generating unit 1122 may estimate a movement path of a speckle in view of the ultrasound image data, and may generate a speckle tracking image that expresses movement of the speckle by using an arrow or a color, based on the estimated movement path of the speckle.

Furthermore, the image generating unit 1122 may display various types of additional information in the form of text or graphical image on the ultrasound image. For example, the image generating unit 1122 may add one or more annotations, which are related to some or all contents of the ultrasound image, to the ultrasound image. That is, the image generating unit 1122 may analyze the ultrasound image, and may recommend the one or more annotations that are related to some or all contents of the ultrasound image, based on a result of the analysis. Also, the image generating unit 1122 may add one or more annotations that are selected by a user to the ultrasound image.

The image processing unit 1120 may extract a region of interest from the ultrasound image by using an image processing algorithm. Here, the image processing unit 1120 may add a color, a pattern, or a boundary to the region of interest.

The user input unit 1200 means a unit by which the user (e.g., a sonographer) inputs data so as to control the ultrasound apparatus 1000. For example, the user input unit 1200 may be formed of, but is not limited to, a key pad, a dome switch, a touch pad (a touch capacitive type touch pad, a pressure resistive type touch pad, an infrared beam sensing type touch pad, a surface acoustic wave type touch pad, an integral strain gauge type touch pad, a Piezo effect type touch pad, or the like), a track ball, a jog switch, or the like. The user input unit 1200 may further include various input units such as an electrocardiogram measurement module, a breathing measurement module, a voice recognition sensor, a gesture recognition sensor, a fingerprint recognition sensor, an iris recognition sensor, a depth sensor, a distance sensor, etc.

In the present embodiment, the user input unit 1200 may sense not only an actual touch but also may sense a proximate touch. The user input unit 1200 may sense a touch input (e.g., a touch & hold input, a tap input, a double tap input, a flick input, etc.) with respect to the ultrasound image. Also, the user input unit 1200 may sense a drag input dragged from a point where the touch input is sensed. The user input unit 1200 may sense multi-touch inputs (e.g., a pinch) with respect to at least two points on the ultrasound image.

The user input unit 1200 may receive an input of selecting the region of interest in the B mode image. For example, the user input unit 1200 may receive a user input of selecting an area including a needle tip, as the region of interest.

The controller 1300 controls all operations of the ultrasound apparatus 1000. For example, the controller 1300 may generally control the ultrasound image data obtainer 1100, the user input unit 1200, the communication unit 1400, the memory 1500, and the display 1600.

The controller 1300 may control the ultrasound image data obtainer 1100 to obtain first B mode image data and first Doppler data about the target object 10 to which the medicine is injected. Here, the controller 1300 may detect a first area of the target object 10 from which the first Doppler data is obtained, and may determine a first diffusion boundary of the medicine based on the detected first area. For example, the controller 1300 may determine an outside area of the first area from which the first Doppler data is obtained, as the first diffusion boundary of the medicine.

Here, when a speed value included in the first Doppler data is equal to or greater than a threshold value, the controller 1300 may detect the first area from which the first Doppler data is obtained.

The controller 1300 may detect a partial area of the first area in which the speed value included in the first Doppler data is equal to or greater than the threshold value, and may determine an outside area of the partial area, as the first diffusion boundary of the medicine.

The controller 1300 may control the ultrasound image data obtainer 1100 to obtain second Doppler data about the target object 10 after an elapse of a preset time, and may detect a second area from which the second Doppler data is obtained. Here, the controller 1300 may determine a second diffusion boundary of the medicine, based on the detected second area.

When Doppler data about the target object 10 is no longer obtained, the controller 1300 may store information about the first diffusion boundary in the memory 1500.

When second B mode image data about the target object 10 is obtained, the controller 1300 may compare the first B mode image data with the second B mode image data. If similarity between the first B mode image data and the second B mode image data is less than a preset value, the controller 1300 may store the information about the first diffusion boundary in the memory 1500.

The controller 1300 may detect a diffusion boundary of the medicine by using a speckle tracking algorithm. For example, the controller 1300 may control the ultrasound image data obtainer 1100 to obtain the first and second B mode images of the target object 10 to which the medicine is injected. Also, the controller 1300 may estimate a first movement path of at least one speckle included in the first B mode image, based on a result of comparison between a first speckle pattern included in the first B mode image and a second speckle pattern included in the second B mode image. For example, the controller 1300 may obtain a correlation between the first speckle pattern and the second speckle pattern, and may estimate the first movement path of the at least one speckle by using the correlation.

The controller 1300 may receive an input of selecting a region of interest via the user input unit 1200, and may compare the first speckle pattern included in the region of interest of the first B mode image with the second speckle pattern included in the region of interest of the second B mode image.

The controller 1300 may determine the first diffusion boundary of the medicine, based on the first movement path of the at least one speckle. For example, the controller 1300 may determine a first movement area including the first movement path of the at least one speckle, and may determine an outside area of the first movement area, as the first diffusion boundary of the medicine.

The controller 1300 may determine whether the first movement area is equal to or greater than a preset area. As a result of the determination, when the first movement area is equal to or greater than the preset area, the controller 1300 may determine an outside area of the first movement area, as the first diffusion boundary of the medicine.

The controller 1300 may control the ultrasound image data obtainer 1100 to obtain a third B mode image of the target object 10. Here, the controller 1300 may estimate a second movement path of the at least one speckle included in the second B mode image, based on a result of comparison between the second speckle pattern included in the second B mode image and a third speckle pattern included in the third B mode image.

The controller 1300 may determine the second diffusion boundary of the medicine, based on the second movement path, and may control the display 1600 to display the second diffusion boundary of the medicine on the third B mode image.

When a movement distance of the at least one speckle included in the second B mode image is less than a threshold value, the controller 1300 may store the information about the first diffusion boundary in the memory 1500.

The controller 1300 may compare the second B mode image and the third B mode image, and as a result of the comparison, if a similarity between the second B mode image and the third B mode image is less than a preset value, the controller 1300 may store the information about the first diffusion boundary in the memory 1500.

The communication unit 1400 may include one or more configuring elements that allow communication between the ultrasound apparatus 1000 and the server 2000, the ultrasound apparatus 1000 and the first device 3000, and the ultrasound apparatus 1000 and the second device 4000. For example, the communication unit 1400 may include a short-distance communication module 1410, a wired communication module 1420, a mobile communication module 1430, or the like.

The short-distance communication module 1410 is a module for short-distance communication within a predetermined distance. The short-distance communication may include, but is not limited to, a wireless LAN (Wi-Fi), Bluetooth, Bluetooth low energy (BLE), Ultra Wideband (UWB), ZigBee, near field communication (NFC), Wi-Fi Direct (WFD), and infrared Data Association (IrDA).

The wired communication module 1420 indicates a module for communication performed by using an electrical signal or an optical signal. A wired communication technology may include a pair cable, a coaxial cable, an optical fiber cable, Ethernet, or the like.

The mobile communication module 1430 exchanges a wireless signal with at least one of a base station, an external device (e.g., the first device 3000 and the second device 4000), and the server 2000 on a mobile communication network. Here, the wireless signal may include various types of data according to communication of a sound call signal, a video call signal, or a text/multimedia message.

The communication unit 1400 may communicate with the external device (e.g., the first device 3000 or the second device 4000) or the server 2000 via a wireless or wired network 30. The communication unit 1400 may exchange data with a hospital server or other medical apparatuses in a hospital connected via a Picture Archiving and Communication System (PACS). Also, the communication unit 1400 may perform data communication according to a Digital Imaging and Communications in Medicine (DICOM) standard.

The communication unit 1400 may transmit and receive data such as the ultrasound image, the ultrasound image data, Doppler image data, etc. of the target object 10 which are related to diagnosing the target object 10, via the network 30. Also, the communication unit 1400 may transmit and receive a medical image captured by another medical apparatus such as CT, MRI, X-ray, etc. Furthermore, the communication unit 1400 may receive information about a diagnosis history, a treatment schedule, etc. about a patient from the server 2000 and thus may use the information in diagnosing the target object 10.

The memory 1500 may store a program for processing the controller 1300, or may store a plurality of pieces of data (e.g., the ultrasound image, information about the diffusion boundary of the medicine, examinee information, probe information, a body marker, or the like) that are input/output.

The memory 1500 may include a flash memory-type storage medium, a hard disk-type storage medium, a multimedia card micro-type storage medium, a card type memory (e.g., an SD card memory or an XD card memory), a Random Access Memory (RAM), a Static Random Access Memory (SRAM), a Read-Only Memory (ROM), an Electrically Erasable Programmable Read-Only Memory (EEPROM), a Programmable Read-Only Memory (PROM), a magnetic memory, a magnetic disc, and an optical disc. Also, the ultrasound apparatus 1000 may operate a web storage system that performs a storing function of the memory 1500 over the Internet.

The display 1600 displays and outputs information that is processed by the ultrasound apparatus 1000. For example, the display 1600 may display the ultrasound image or may display a user interface (UI) or a graphical user interface (GUI) related to a control panel.

The display 1600 may display the first diffusion boundary of the medicine on the B mode image that is generated by using the first B mode image data. For example, the display 1600 may display the first diffusion boundary of the medicine by using a line having a preset form. Also, the display 1600 may transparently or translucently display, on the B mode image, the first Doppler image that is generated based on the first Doppler data.

The display 1600 may display the first diffusion boundary of the medicine and the second diffusion boundary of the medicine on the B mode image. Also, the display 1600 may display a third diffusion boundary of the medicine on the B mode image. For example, the display 1600 may determine a third area by combining the first area from which the first Doppler data is obtained and the second area from which the second Doppler data is obtained, and may mark an outside area of the third area, as the third diffusion boundary of the medicine.

When a region of interest is set, the display 1600 may display the first diffusion boundary, the second diffusion boundary, or the third diffusion boundary in the region of interest.

The display 1600 may display, on the second B mode image, the first diffusion boundary of the medicine which is determined by using a speckle tracking algorithm. Here, the display 1600 may transparently or translucently display a speckle tracking image that is generated based on a movement path of the at least one speckle.

The display 1600 may provide numerical data (e.g., a diameter, a circumference, an area, a volume, etc.) about a diffusion range of the medicine on the B mode image. The display 1600 may provide comparison data (e.g., an error rate) obtained by comparing an estimated diffusion range of the medicine with an actual diffusion range of the medicine.

When the display 1600 and a touch pad form a mutual layer structure and then are formed as a touch screen, the display 1600 may be used as both an output device and input device. The display 1600 may include at least one of a liquid crystal display (LCD), a thin film transistor-liquid crystal display (TFT-LCD), an organic light-emitting diode (OLED) display, a flexible display, a 3D display, and an electrophoretic display. Also, according to a type of the ultrasound apparatus 1000, the ultrasound apparatus 1000 may include at least two displays.

One or more embodiments of the present invention may also be embodied as programmed commands to be executed in various computer units, and then may be recorded in a computer-readable recording medium. The computer-readable recording medium may include one or more of the programmed commands, data files, data structures, or the like. The programmed commands recorded to the computer-readable recording medium may be particularly designed or configured for one or more embodiments of the present invention or may be well known to one of ordinary skill in the art. Examples of the computer-readable recording medium include magnetic media including hard disks, magnetic tapes, and floppy disks, optical media including CD-ROMs and DVDs, magneto-optical media including floptical disks, and hardware designed to store and execute the programmed commands in ROM, RAM, a flash memory, and the like. Examples of the programmed commands include not only machine code generated by a compiler but also include a high-level programming language to be executed in a computer by using an interpreter.

According to the one or more embodiments of the present invention, the ultrasound apparatus 1000 marks a diffusion boundary of medicine and thus allows a user to check whether the medicine is correctly injected into a target structure in a target object. The user may check the diffusion boundary of the medicine and thus may not inject an unnecessary amount of the medicine into the target object.

It should be understood that the exemplary embodiments described herein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A method of marking a diffusion boundary of medicine, the method performed by an ultrasound apparatus and comprising:
   obtaining first B mode image data and first Doppler data about a target object to which the medicine is injected;
   obtaining second Doppler data about the target object, after the first B mode image data and the first Doppler data are obtained and then a preset time elapses;
   detecting a first area of the target object from which the first Doppler data is obtained and a second area from which the second Doppler data is obtained;
   determining a first diffusion boundary of the medicine, based on the first area, and determining a second diffusion boundary of the medicine, based on the second area;
   marking the first diffusion boundary of the medicine and the second diffusion boundary of the medicine on a B mode image that is generated by using the first B mode image data; and
   displaying, on the B mode image, comparison data obtained by comparing an estimated diffusion range of the medicine with an actual diffusion range of the medicine,
   wherein the comparison data comprises:

estimating the diffusion range of the medicine, based on at least one of information about a position to which the medicine is injected and an injection amount of the medicine, obtaining the actual diffusion range of the medicine, based on the first area and the second area, and comparing the estimated diffusion range of the medicine with the actual diffusion range of the medicine, and the method further comprises displaying the comparison data including an error rate of the estimated diffusion range of the medicine for the actual diffusion range of the medicine.

2. The method of claim 1, wherein the first Doppler data comprises at least one of color Doppler image data and power Doppler image data.

3. The method of claim 1, wherein, when a speed value comprised in the first Doppler data is equal to or greater than a threshold value, the detecting of the first area comprises detecting the first area from which the first Doppler data is obtained.

4. The method of claim 1, wherein, in the determining of the first diffusion boundary, an outside area of the first area from which the first Doppler data is obtained is determined as the first diffusion boundary of the medicine.

5. The method of claim 1, wherein the determining of the first diffusion boundary comprises:
detecting a partial area of the first area where a speed value comprised in the first Doppler data is equal to or greater than a threshold value; and
determining an outside area of the partial area, as the first diffusion boundary of the medicine.

6. The method of claim 1, wherein the marking of the first diffusion boundary comprises marking the first diffusion boundary of the medicine by using a line having a preset form.

7. The method of claim 1, wherein the marking of the first diffusion boundary comprises transparently or translucently displaying a first Doppler image that is generated based on the first Doppler data.

8. The method of claim 1, further comprising:
determining a third area by combining the first area and the second area;
determining an outside area of the third area, as a third diffusion boundary of the medicine; and
marking the third diffusion boundary of the medicine on the B mode image.

9. The method of claim 1, wherein the marking of the first diffusion boundary comprises:
receiving an input of selecting a region of interest in the B mode image; and
marking the first diffusion boundary in the region of interest.

10. The method of claim 1, further comprising, when Doppler data about the target object is no longer obtained, storing information about the first diffusion boundary.

11. The method of claim 1, further comprising:
obtaining second B mode image data about the target object;
comparing the first B mode image data and the second B mode image data; and
when a similarity between the first B mode image data and the second B mode image data is less than a preset value, storing information about the first diffusion boundary.

12. The method of claim 1, further comprising providing, on the B mode image, at least one of numerical data about a diffusion range of the medicine.

13. An ultrasound apparatus comprising:
an ultrasound image data obtainer configured to obtain first B mode image data and first Doppler data about a target object to which medicine is injected, and second Doppler data about the target object after the first B mode image data and the first Doppler data are obtained and then a preset time elapses;
a controller configured to detect a first area of the target object from which the first Doppler data is obtained, and a second area from which the second Doppler data is obtained, and configured to determine a first diffusion boundary of the medicine, based on the first area, and a second diffusion boundary of the medicine, based on the second area; and
a display configured to mark the first diffusion boundary of the medicine and the second diffusion boundary of the medicine on a B mode image that is generated by using the first B mode image data, and display, on the B mode image, comparison data obtained by comparing an estimated diffusion range of the medicine with an actual diffusion range of the medicine,
wherein the controller further configured to
estimate the diffusion range of the medicine, based on at least one of information about a position to which the medicine is injected and an injection amount of the medicine,
obtain the actual diffusion range of the medicine, based on the first area and the second area,
compare the estimated diffusion range of the medicine with the actual diffusion range of the medicine,
wherein the display further configured to display the comparison data including an error rate of the estimated diffusion range of the medicine for the actual diffusion range of the medicine.

14. A non-transitory computer-readable recording medium having recorded thereon a program for executing the method of claim 1.

* * * * *